United States Patent
Cabantchik et al.

(10) Patent No.: US 7,090,995 B2
(45) Date of Patent: Aug. 15, 2006

(54) MOLECULES AND METHODS USING SAME FOR MEASURING NON-TRANSFERRIN BOUND IRON

(75) Inventors: Ioav Zvi Cabantchik, Har Adar (IL); William Breuer, HaEla (IL); Breno P. Esposito, Sao Paulo (BR)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 367 days.

(21) Appl. No.: 10/283,343

(22) Filed: Oct. 30, 2002

(65) Prior Publication Data

US 2003/0104491 A1   Jun. 5, 2003

Related U.S. Application Data

(63) Continuation-in-part of application No. PCT/IL01/00384, filed on Apr. 29, 2001.

(30) Foreign Application Priority Data

Apr. 30, 2000  (IL) .................................. 135884

(51) Int. Cl.
 *C12Q 1/34* (2006.01)
 *G01N 33/20* (2006.01)
(52) U.S. Cl. .......................... 435/18; 436/74
(58) Field of Classification Search ................ 435/18; 436/74
 See application file for complete search history.

(56) References Cited

OTHER PUBLICATIONS

Saito "Method of determination of iron in the form of ferrioxamine in urine" Rinsho Kagaku 1(1): 100-2 (1971).*
Singh et al., "A direct method for quantification of non-transferrin-bound iron", Analytical Biochemistry 186(2): 320-3 (1990).*
Zhang et al., "An improved simple colorimetric method for quantitation of non-transferrin-bound iron in serum", Biochemistry an Molecular Biology International 35 (3) 635-41(1995).*
Loreal et al., "Determination of non-transferrin-bound iron in genetic hemochromatosis using a new HPLC-based method", Journal of Hepatology 32(5) : 727-733 (2000).*
Breuer et al., "The assessment of serum nontransferrin-bound iron in chelation therapy and iron supplementation", Blood 95(9) 2975-82 (2000).*
Breuer et al., "Desferrioxamine-chelatable iron, a component of serum non transferrin-bound iron, used for assessing chelation therapy", Blood 97(3) : 792-98 (2001).*
Breuer et al., "A fluorescence-based one-step assay for serum non-transferrin-bound iron", Analytical Biochemistry 299(2) :194-202 (2001).*

* cited by examiner

*Primary Examiner*—Sandra E. Saucier

(57) ABSTRACT

A molecule suitable for use as an indicator of free iron levels in a biological sample, the molecule including an iron binding moiety and a signal generating moiety, wherein an intensity of the signal generated by the signal generating moiety is related to an amount of the iron bound by the iron binding moiety.

20 Claims, 16 Drawing Sheets

(13 of 16 Drawing Sheet(s) Filed in Color)

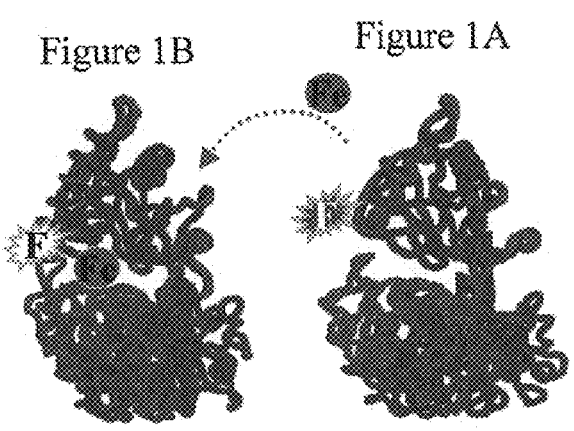
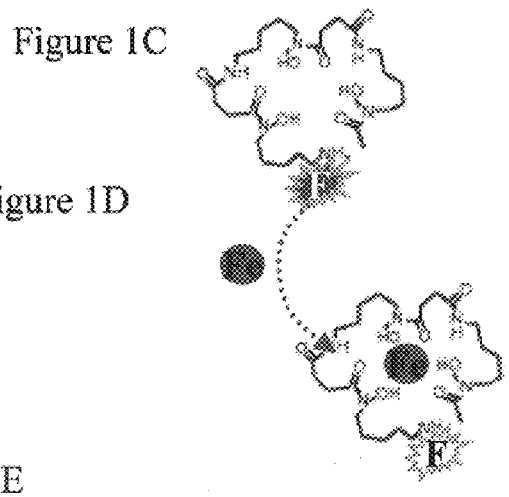
Figure 1B  Figure 1A  Figure 1C
Figure 1D
Figure 1E
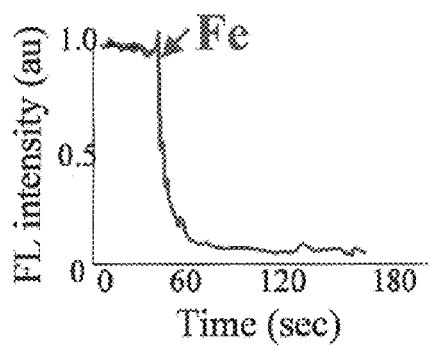

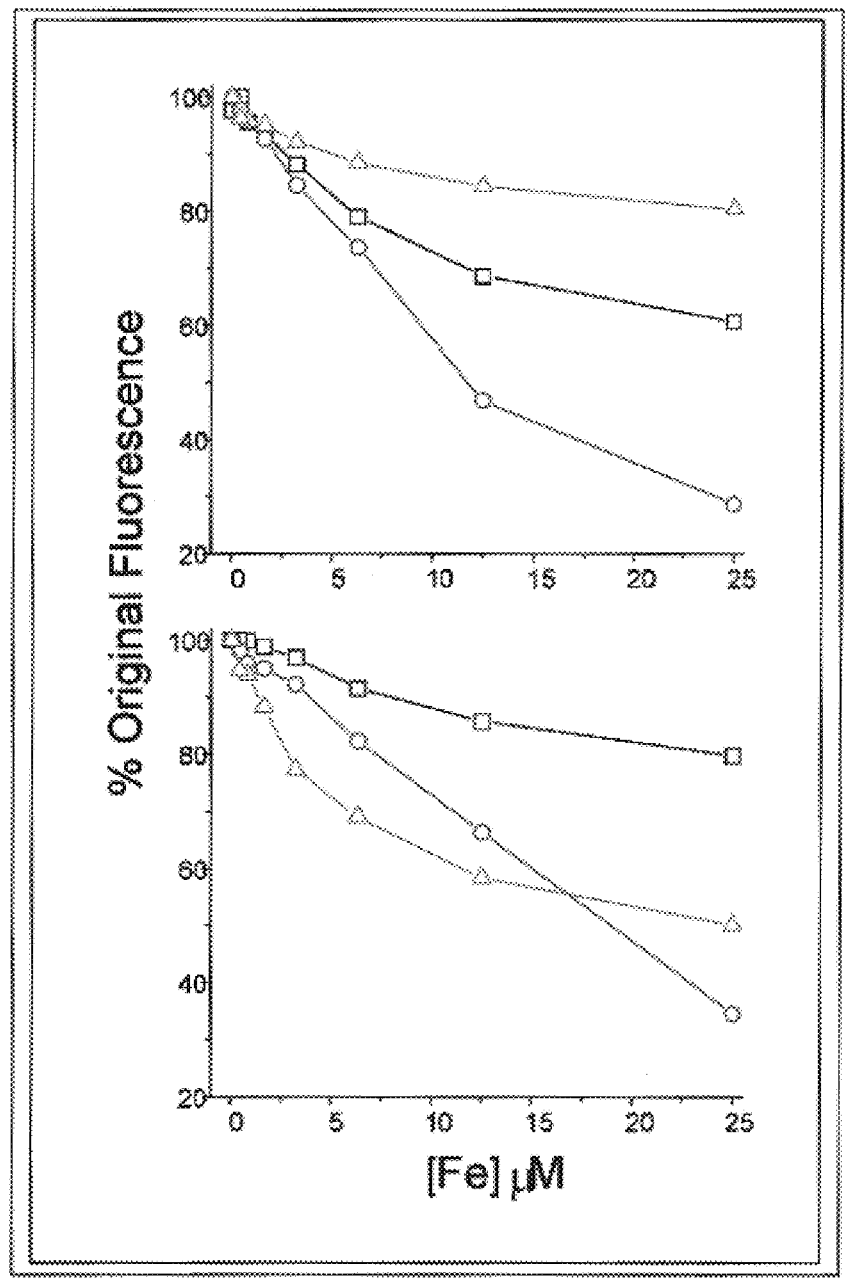

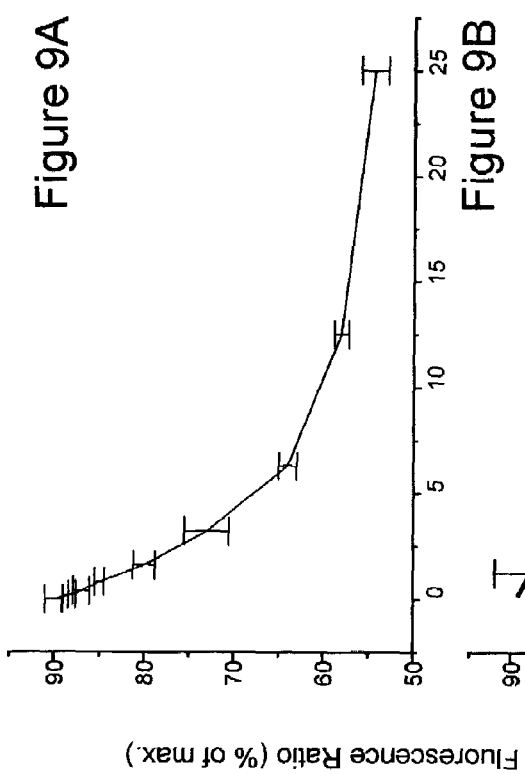
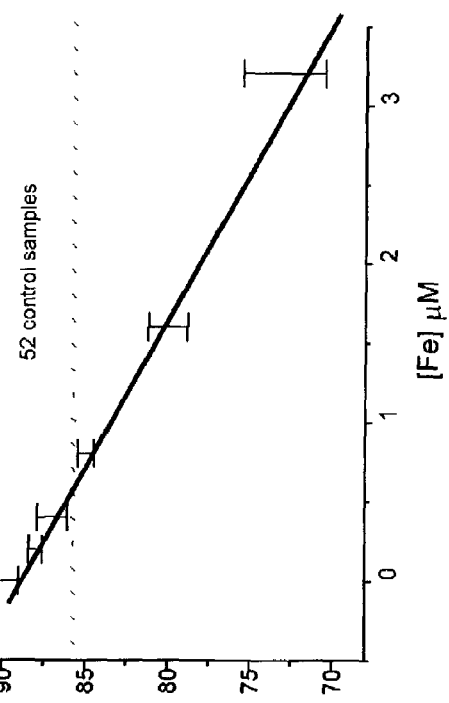
Figure 9A
Figure 9B

MOLECULES AND METHODS USING SAME FOR MEASURING NON-TRANSFERRIN BOUND IRON

This is a continuation-in-part of PCT Application No. IL01/00384, filed Apr. 29, 2001, which claims the benefit of priority from Israeli Patent Application No. 135884, filed Apr. 30, 2000.

FIELD AND BACKGROUND OF THE INVENTION

The present invention relates to novel molecules, which can be used to measure non-transferrin-bound iron. Specifically, the molecules of the present invention can be used to diagnose disorders associated with abnormal levels of free iron, such as hereditary hemachromatosis.

The presence of non-transferrin-bound iron (NTBI) in the circulation is a pathological phenomenon, which occurs in patients with iron-overload conditions. NTBI is absent from healthy individuals where virtually all of the serum iron is bound to the iron-carrier protein, transferrin. However, in iron-overloaded individuals, the iron binding capacity of transferrin is overwhelmed, resulting in the adsorption of the excess iron to various proteins and possibly other molecules in the serum. This iron so adsorbed is collectively referred to as NTBI.

Generally, chronic iron-overload accompanied by NTBI occurs as a result of pathological conditions associated with specific diseases. Illustrative examples of such conditions include: 1) repeated transfusions, which are required by patients with various hemolytic diseases, hemoglobinopathics (among which the most common is thalassemia) or other forms of anemia whose treatment demands blood transfusions and/or iron infusion (e.g. dialysis patients) and 2) ant inherited defect causing excess iron absorption, called Hereditary Hemachromatosis. Transient, reversible NTBI can also appear in the circulation of patients undergoing chemotherapy, heart bypass operations and other conditions where large amounts of iron, such as from hemoglobin catabolism, are suddenly released into the circulation. NTBI was also found in patients receiving dialysis who are treated for anemia with erythropoietin and intravenous iron supplements.

Accurate assessment of NTBI concentration is critical for a number of therapeutic applications. Patients suffering from Iron-overload are often prescribed a regimen of Iron chelating agents, whose efficacy hinges on accurate NTBI quantification. Low-level NTBI detection is critical for accurate diagnosis of Iron-overload [Sham, et al., Asymptomatic hemochromatosis subjects: genotypic and phenotypic profiles. Blood (2000), Vol. 96: 3707–3711]. The availability of a rapid and inexpensive NTBI-test would additionally provide screening methods for populations at high-risk for from overload. Since a high frequency of genetic mutation causing Hereditary Hemachromatosis (1 in 8 are heterozygous) exists in Northern European and American populations, and a doubling of the frequency is observed in some African and African-American populations, such screening procedures would clearly impact a large segment of the population. Further, Hereditary Hemachromatosis is often initially misdiagnosed due to a lack of definitive symptoms in the first decades of life, with evidently normal transferrin-iron saturation levels.

To date, there is no single convenient and reliable method for detection of Iron-overload and for specific quantification of NTBI. Iron-overload is most often diagnosed by the estimation of total serum iron via chemical/physicochemical methods, determination of the percent transferrin-iron saturation, or serum iron-binding capacity, by measuring high-affinity binding of radioactive iron to serum components or by determining circulating ferritin levels by immunoassay. While these assays are effective in detecting severe Iron-overload, they often fail to detect low-moderate Iron overload, and additionally have been known to produce false positives.

Currently, a few methods exist for determining NTBI in biological samples. One method [Singh, S., Hider, R. C. and Porter, J. B. (1990) Anal. Biochem. 186, 320–323] utilizes HPLC isolation and incorporation of an iron chelator, deferriprone (or L1), which forms a colored complex that is stoichiometric when in contact with sample NTBI, thereby quantifying the amount of iron in the sample.

The three main drawbacks of this method are its cost, its cumbersome nature, which makes it difficult to set up in non-specialized laboratories, and its relatively low throughput efficiency.

A second method [Evans, P. J. and Halliwell, B. (1994) Methods Enzymol., 233, 82–89] employs the use of the antibiotic bleomycin, which combines with NTBI, but not with transferrin-bound iron, to form highly reactive complexes which generate DNA cleavage products. The relative amount of DNA cleavage product is proportional to the amount of input NTBI and is quantified by a thiobarbituric acid test. The method, however, tends to overestimate NTBI and may give false positive results, limiting effective clinical application.

World patent application No. 00/36422 submitted by the applicant, incorporated fully herein by reference, describe an alternative method for determining the concentration of a free metal ion, in particular non-transferrin bound iron (NTBI), in biological samples. The method consists of incubating a sample suspected of containing NTBI with a surface coated with a polymer-conjugated form of an Iron chelator, for example, a desferrioxamine (DFO) polymer, enabling sample Iron capture by the chelator. Following Iron capture, a labeled moiety containing bound Iron that can be captured by the Iron chelator is added and the concentration of NTBI in samples tested is obtained from the change in label signal obtained with the serum sample relative to control which is regarded as nominally NTBI-free.

The above NTBI detection assay provides an effective process, however the presence of several discrete steps within the assay result in a labor-intensive process, that may not be optimal for all potential clinical settings where the precision and simplicity of the assay are critical for efficient execution.

The use of fluorescent probes in detection systems for clinical applications is highly desirable. Fluorescent probe incorporation in clinical assays typically allows for simple, high-throughput efficiency detection systems. The use of fluorescent-labeled probes in developing the aforementioned NTBI detection system has been problematic, however. Coupling of fluorescent probe to the chelator results in a probe that is sensitive, by its nature, to the environment, hence affected by color, turbidity, pH, ionic strength) of solutions utilized in the assay system, confounding assay readout results.

Further confounding issues in the accurate determination of NTBI in biological samples is poor detection of aggregated Iron, present in the samples, resulting in a lower estimation than the actual amount of NTBI in a given biological sample.

The presence of apo-Transferrin, or Transferrin not bound to Iron, in biological samples, provides yet another source of error in attempting to determine absolute levels of NTBI. Since apo-Transferrin is universally found in biological samples, except in cases of extreme iron-overload where the Transferrin is 100% iron-saturated, actual NTBI in vivo may in fact, bind to apo-Transferrin in the assay sample, resulting in a low estimation of in vivo NTBI levels.

While it is a logical consideration to utilize fluorescein-labeled Transferrin as a means of detecting NTBI within a given sample, the existing art for conjugating fluorescein to transferrin (Egan T J: Fluorescence energy transfer studies on fluoresceinated human serum transferrin. Identification of the possible fluoresceination sites. S. Aft. J. Sci. 89: 446–50) conjugated the fluorescent label to iron-loaded Transferrin. A major drawback to fluorescein-transferrin prepared by this protocol is its failure to detect iron appropriately when measures are taken to inactivate endogenous apo-Transferrin within samples, resulting in a lower level of NTBI than what is actually present in vivo. Utilization of Gallium compounds for inactivation of endogenous apo-Transferrin with this protocol result in inaccurate detection of NTBI, and hence does not provide an accurate assay system.

There is thus a widely recognized need for, and it would be highly advantageous to have, an NTBI detection assay, devoid of the above limitations. A highly sensitive assay system for the quantification of NTBI that is cost-effective, providing high-throughput efficiency, yet not compromised for accuracy and sensitivity has broad clinical application in both the diagnosis and validation of treatment regimens for Iron-overload conditions.

SUMMARY OF THE INVENTION

According to one aspect of the present invention there is provided a molecule suitable for use as an indicator of free iron levels in a biological sample, the molecule comprising an iron binding moiety and a signal generating moiety, wherein an intensity of the signal generated by the signal generating moiety is related to an amount of the iron bound by the iron binding moiety.

According to another aspect of the present invention there is provided a method of quantifying free iron levels in a biological fluid, the method comprising: (a) contacting a sample of the biological fluid with an indicator including an iron binding moiety and signal generating moiety, wherein an intensity of the signal generated by the signal generating moiety is related to an amount of the iron bound by the iron binding moiety; and (b) detecting and quantifying the signal thereby quantifying free iron levels in the biological sample.

According to yet another aspect of the present invention there is provided a method of determining a presence or absence of a disorder associated with abnormal levels of free iron in a biological fluid of a subject the method comprising: (a) obtaining a sample from the biological fluid of the subject; (b) contacting the sample with an indicator including an iron binding moiety and signal generating moiety, wherein an intensity of the signal generated by the signal generating moiety is related to an amount of the iron bound by the iron binding moiety; and (c) detecting and quantifying the signal thereby quantifying free iron levels in the biological fluid and determining in the subject a presence or absence of the disorder associated with abnormal free iron levels.

According to still another aspect of the present invention there is provided a method of identifying putative regulators of free iron levels, the method comprising: (a) exposing a cell to a plurality of agents; and (b) identifying an agent of the plurality of agents which induces an alteration in free iron levels in growth medium of the cell as a result of exposure of the cell thereto, including: (i) contacting the growth medium with an indicator including an iron binding moeity and signal generating moeity, wherein an intensity of the signal generated by the signal generating moeity is related to an amount of the iron bound by the iron binding moeity; and (ii) detecting and quantifying the signal thereby quantifying free iron levels in the growth medium, thereby identifying the putative regulators of free iron levels.

According to an additional aspect of the present invention there is provided a kit for determining a presence or an absence of a disorder associated with abnormal levels of free iron in a biological fluid of a subject the kit comprising an indicator including an iron binding moiety and a signal generating moiety, wherein an intensity of the signal generated by the signal generating moiety is related to an amount of the iron bound by the iron binding moiety.

According to further features in preferred embodiments of the invention described below, the kit father comprising manganate.

According to yet an additional aspect of the present invention there is provided a method of quantifying redox active iron levels in a biological fluid, the method comprising: (a) contacting a sample of the biological fluid with a reducing agent, to obtain redox active iron; (b) contacting the sample with a detector molecule selected capable of measurable activation upon contact with redox active iron reaction products, wherein the measurable activation is related to an amount of the redox active iron reaction product; and (c) quantifying the measurable activation, thereby quantifying redox active iron levels in the biological fluid.

According to still an additional aspect of the present invention there is provided a kit for determining a presence or an absence of a disorder associated with abnormal levels of free iron in a biological fluid of a subject, the kit comprising an indicator including an iron binding moiety and a signal generating moiety, wherein an intensity of the signal generated by the signal generating moiety is related to an amount of the iron bound by the iron binding moiety.

According to a further aspect of the present invention there is provided a method of treating a disorder associated with abnormal levels of free iron in a biological fluid of a subject, the method comprising: (a) determining a level of free iron in the biological fluid of the subject; and (b) treating the disorder according to the level of free iron in the biological fluid of the subject.

According to still further features in the described preferred embodiments the method further comprising obtaining a sample of the biological fluid from the subject prior to step (a).

According to still further features in the described preferred embodiments the method further comprising repeating steps (a)–(b) following a predetermined time period.

According to still further features in the described preferred embodiments wherein the intensity of the signal is stoichiometrically related to the iron bound by the iron binding moeity.

According to still further features in the described preferred embodiments wherein the indicator is a modified apo-transferrin.

According to still further features in the described preferred embodiments wherein the indicator is fluorescein-apo-transferrin.

According to still further features in the described preferred embodiments wherein the signal generating moiety of the modified apo-transferrin is a fluorophore.

According to still further features in the described preferred embodiments wherein the fluorophore is selected from the group consisting of Fluorescein, Rhodamin, nitrobenzfurazan, fluorogenic β-galactosidase and a green fluorescent protein.

According to still further features in the described preferred embodiments wherein the intensity of the signal generated by the modified transferrin is substantially unaffected by apo-transferrin binding metals other than iron.

According to still further features in the described preferred embodiments wherein the signal generating moiety includes a reactive group for binding the iron binding moiety.

According to still further features in the described preferred embodiments wherein the reactive group is selected from the group consisting of dichlorotriazinyl, isothiocyanate, succinimidyl ester sulfonyl chloride.

According to still further features in the described preferred embodiments wherein the dichlorotriazinyl is DTAF.

According to still further features in the described preferred embodiments wherein the iron binding moiety is selected from the group consisting of apo-transferrin, lactoferrin, ovotransferrin, desferrioxamine, phenanthroline, ferritin, porphyrin, EDTA and DPTA.

According to still further features in the described preferred embodiments wherein the indicator is an enzyme.

According to still further features in the described preferred embodiments wherein the enzyme is an aconitase enzyme.

According to still further features in the described preferred embodiments the method further comprising contacting the sample with an apo-transferrin binding metal other than iron prior to step (a).

According to still further features in the described preferred embodiments the apo-transferrin binding metal other than iron is selected from the group consisting of Gallium and Cobalt.

According to still further features in the described preferred embodiments the method further comprising contacting the sample with an iron mobilizing reagent prior to step (a).

According to still further features in the described preferred embodiments wherein the iron mobilizing reagent is selected from the group consisting of sodium-oxalate, nitrilotriaacetate, ascorbate and salicylate.

According to still further features in the described preferred embodiments the method further comprising comparing the signal generated from the sample to the signal generated from a second sample pretreated with an iron chelator prior to step (b).

According to still further features in the described preferred embodiments wherein the iron chelator is the iron binding moiety of the indicator.

According to still further features in the described preferred embodiments wherein the chelator is selected from the group consisting of DPTA, EDTA, HBED and deferriprone.

According to still further features in the described preferred embodiments wherein the biological fluid is selected from the group consisting of blood, serum, plasma, lymph, bile fluid, urine, saliva, sputum, synovial fluid, semen, tears, cerebrospinal fluid, bronchioalveolar lavage fluid, ascites fluid and pus.

According to still further features in the described preferred embodiments the method further comprising removing of endogenous apo-transferrin from the biological fluid prior to step (a).

According to still further features in the described preferred embodiments wherein the removing of endogenous apo-transferrin is effected by: (i) an anti apo-transferrin antibody; and/or an anionic solid phase.

According to still further features in the described preferred embodiments wherein the quantifying the signal is effected against a calibration curve the calibration curve depicting a fluorescence quenching against known iron concentration.

According to still further features in the described preferred embodiments wherein said signal generating moiety is a fluorophore The present invention successfully addresses the shortcomings of the presently known configurations by providing novel molecules and methods using the same for the straightforward, accurate and sensitive identification of free iron levels.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings:

FIGS. 1A–D are schematic descriptions of the fluorescent iron indicator molecules generated according to the teachings of the present invention. Two examples are provided; the fluorescent derivative of DFO, NBD-DFO (FIG. 1C) and its iron bound form (FIG. 1D) and the fluorescent derivative of transferrin, FL-aTF (FIG. 1A) and its iron bound form (FIG. 1B).

FIG. 1E is a graph depicting fluorescence quenching as a function of time following iron binding.

Figure 2:
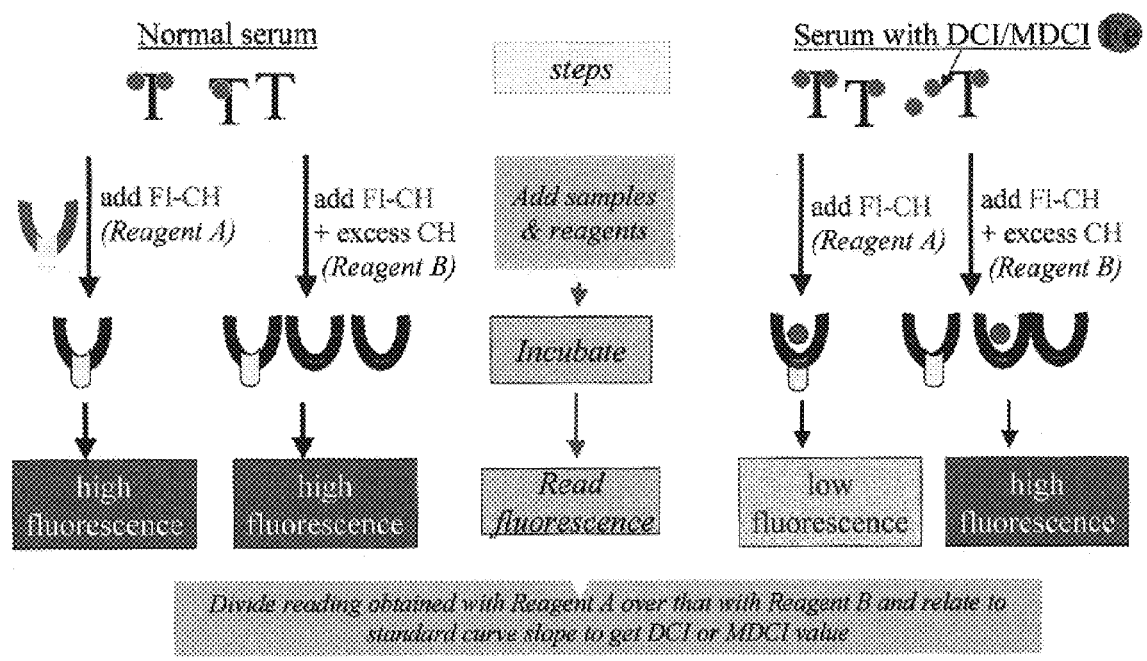

FIG. 2 is a schematic illustration of the basic assay for assessing DCI (directly chelatable iron) or MDCI (mobilizer-dependent chelatable iron) also known as NTBI (non-transferrin bound iron) in plasma and other biological fluids.

These forms of iron are revealed by a change in fluorescence signal following addition of Reagent A (see Example 1 and the Materials and Experimental Methods section of the Examples section for description) versus Reagent 13 (see Example 1 and the Materials and Experimental Methods section of the Examples section for description), whenever the input sample contains the respective forms of DCI or MDCI. The change in fluorescence found with Reagent A relative to that found with Reagent B in equivalent input samples provides a direct measure for DCI or MDCI.

Figure 3:
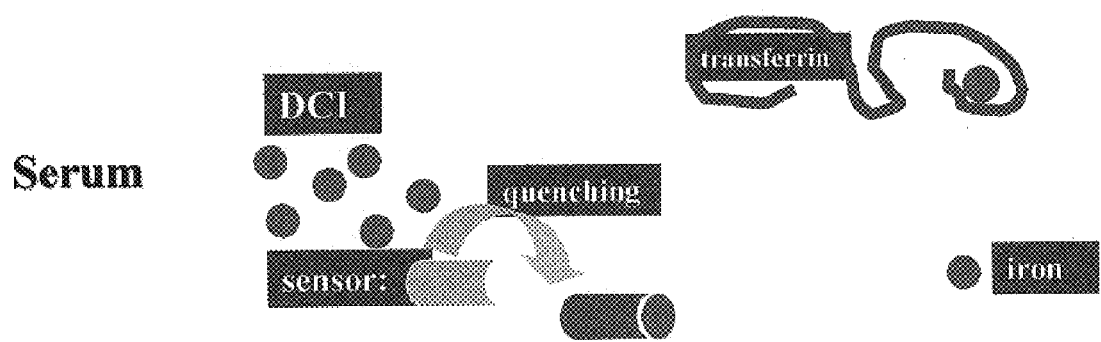

FIG. 3 is a schematic illustration of one embodiment of the method of the present invention used for assessing DCI levels (directly chelatable iron).

Figure 4:
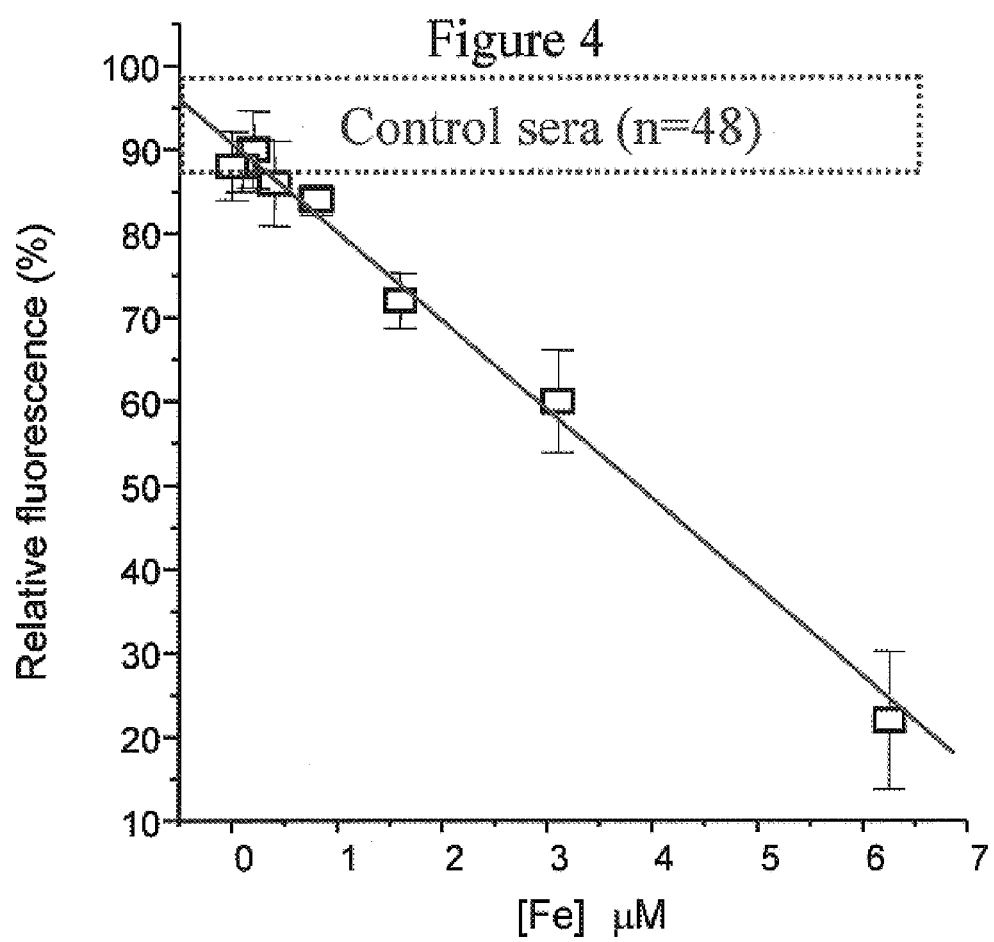

FIG. 4 is a graph depicting a calibration curve, which is essentially a plot of the ratio of fluorescence emitted from samples administered Reagent A versus B, as a function of the value of the input Iron concentration. Control sera shows that serum samples from normal individuals exhibit no detectable DCI levels, i.e., the values obtained with 48 samples from normal individuals were <0.3 µM DC, which is within the error margin of the assay.

Figure 5:
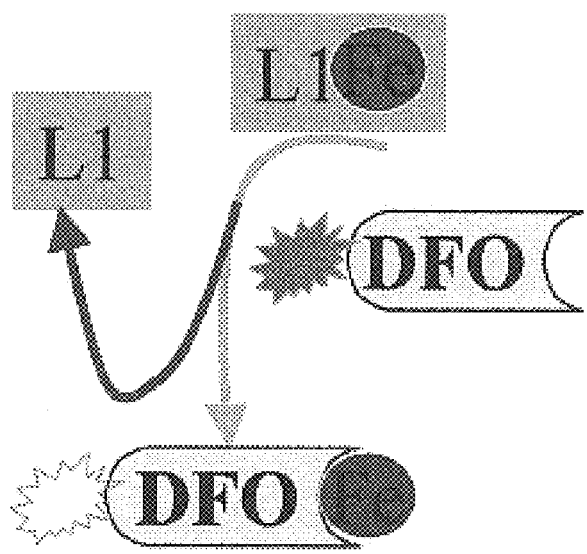

FIG. 5 is a schematic illustration of another embodiment of the method of the present invention directed at detecting iron mobilized from tissues into plasma by chelators such as L1 (also called deferriprone). In the example depicted, a serum sample was taken from a patient following L1 oral administration. The iron mobilized in vivo into the plasma by L1 is transferred to Fl-DFO in vitro, whereupon Fl-DFO's fluorescence is quenched commensurately with the amount of iron transferred. The basic assay is as depicted in FIG. 2.

Figure 6:
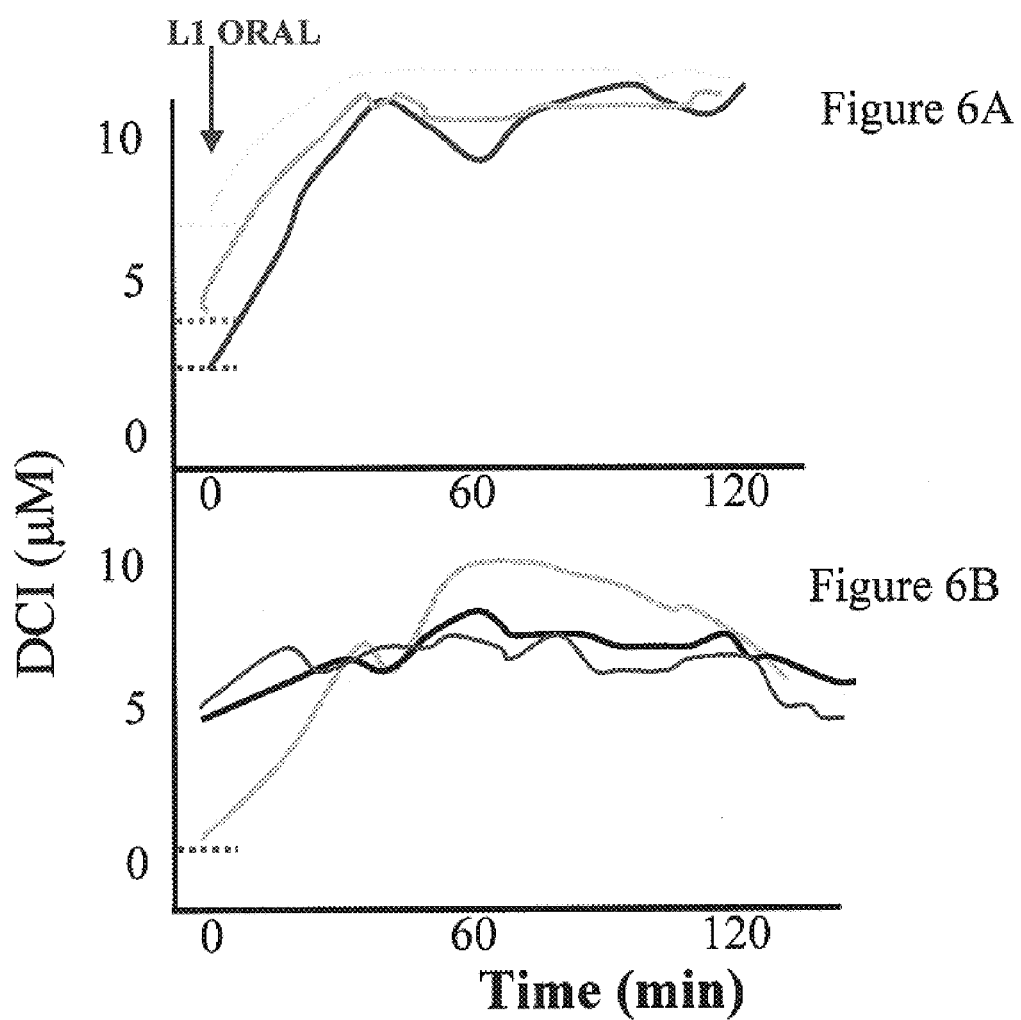

FIGS. 6A–B are graphs depicting the DCI levels in plasma of thalassemic patients (3 from Israel and 3 from Thailand, FIGS. 6B and A, respectively) treated with therapeutic doses of L1 (per os). Sampled were retrieved minutes to hours following L1 administration.

Figure 7:
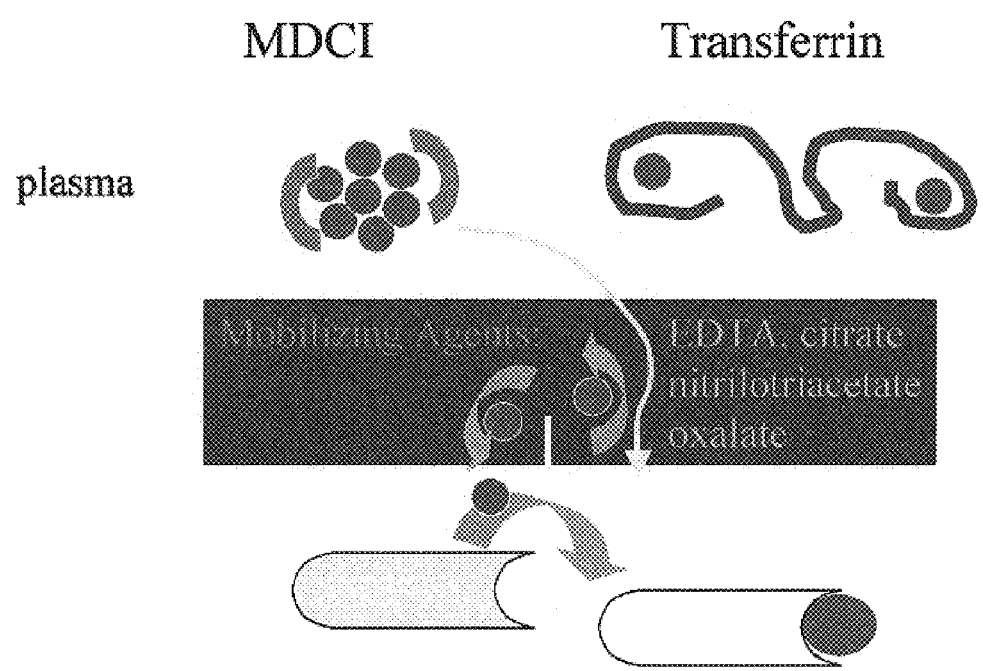

FIG. 7 is a schematic illustration of MDCI (NTBI) detection. MDCI represents all forms of NTBI in plasma and other biological fluids, including those that arc cryptic, namely, not directly chelatable by iron chelators. MDCI incorporates the basic features of DCI, except that reagents A and B are supplemented with iron mobilizing agents (e.g. oxalic acid, salicylic acid, ascorbate, separately or in various combinations) and with Ga salts, in order to prevent the mobilized iron from being transferred to iron binding sites in apo-Transferrin or partially iron-saturated Transferrin.

FIGS. 8A–B graphically depict the ability of two particular preparations of iron-free-transferrin, essentially Fl-TF (FIG. 8A) and Fl-aTF (FIG. 8B), to detect free iron in the presence and absence of oxalate and Gallium [Ga(III)]. 0.6 µM of each of the indicator molecules were tested under three experimental conditions: with no addition (squares), with 10 mM Na-oxalate (circles) and with 10 mM Na-oxalate and 0.1 mM $GaCl_3$ (triangles), Quenching of fluorescence as a function of iron concentration was measured and presented as % Original Fluorescence.

FIGS. 9A–B are graphs depicting calibration of MDCI determination using Fl-aTF. FIG. 9A represents the full range of iron concentrations and FIG. 9B represents the linear range of the calibration curve. The dotted line in FIG. 9b indicates the highest value for MDCI (0.5 µM) that was obtained with serum samples from 52 normal individuals exhibiting no-iron overload. The 0.5 µM value is the error margin of the assay.

Figure 10:
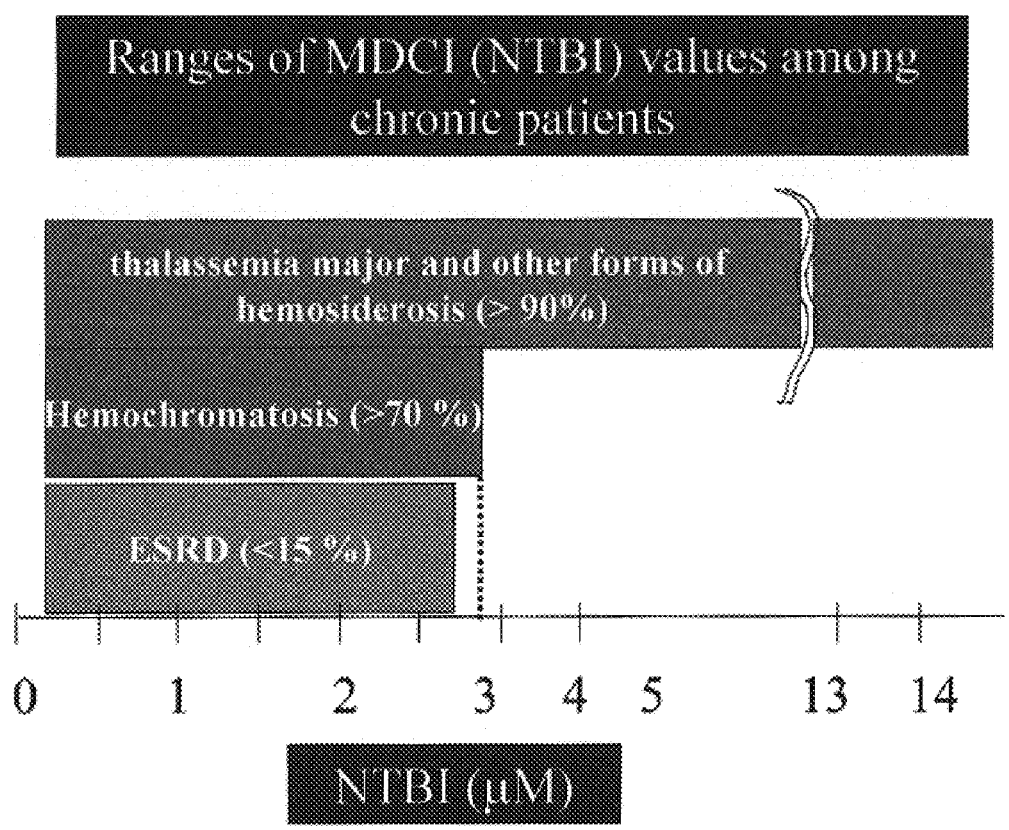

FIG. 10 is a graph illustrating the percent of chronic patients with detectable MDCI levels and the corresponding ranges of MDCI.

Figure 11:
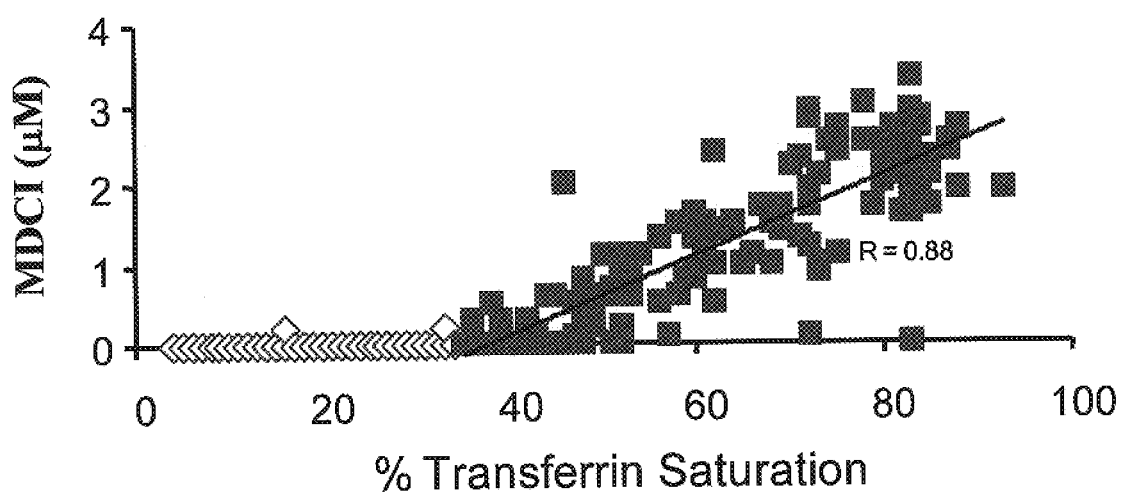

FIG. 11 is a graph illustrating a linear correlation between MDCI levels and transferrin saturation in HH patients. Diamonds indicate transferrin saturation below 35%. Closed squares indicate transferrin saturation above 35%

Figure 12:
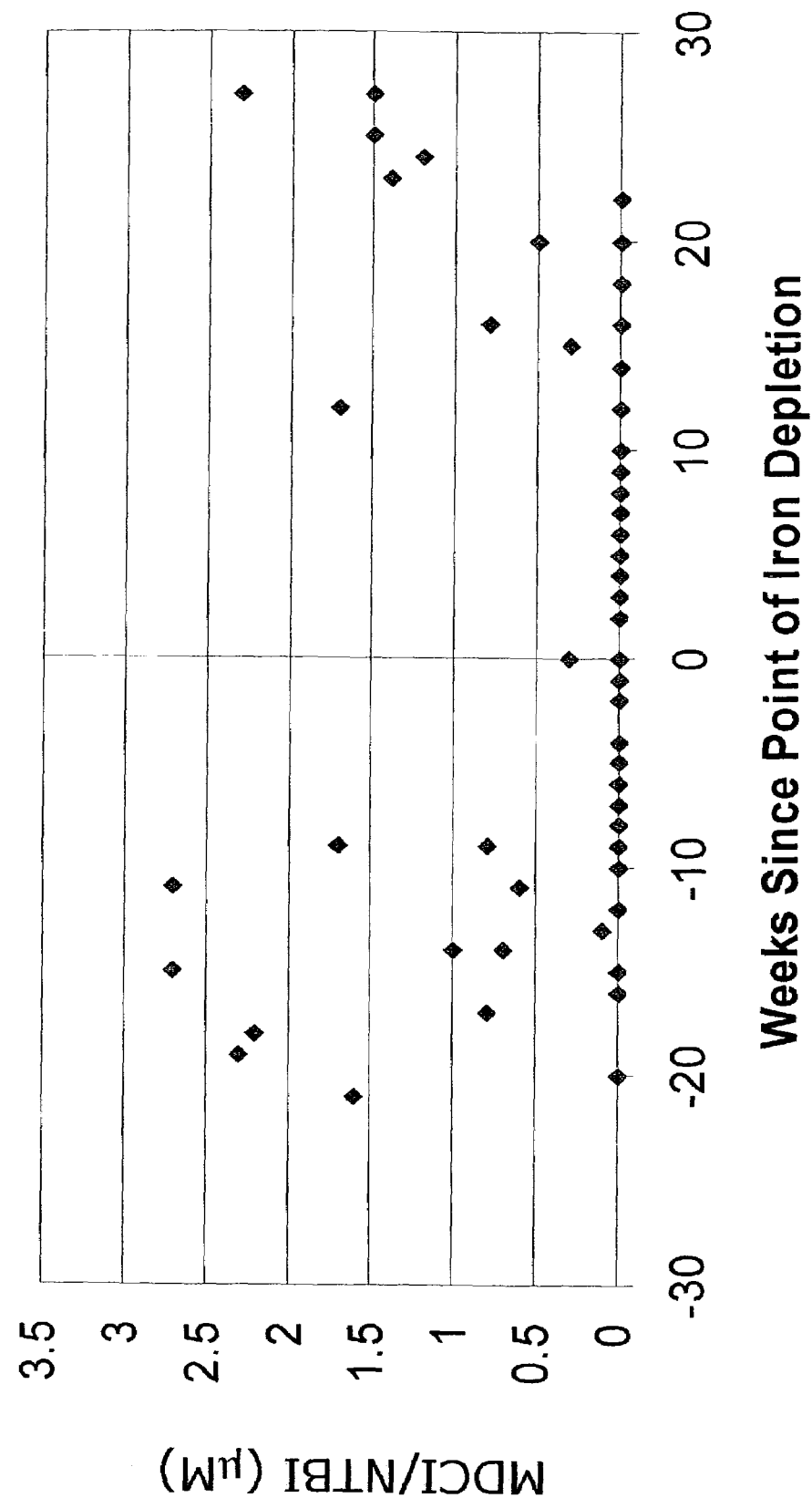

FIG. 12 is a graph illustrating recovery of MDCI levels in HH patients following iron depletion.

Figure 13:
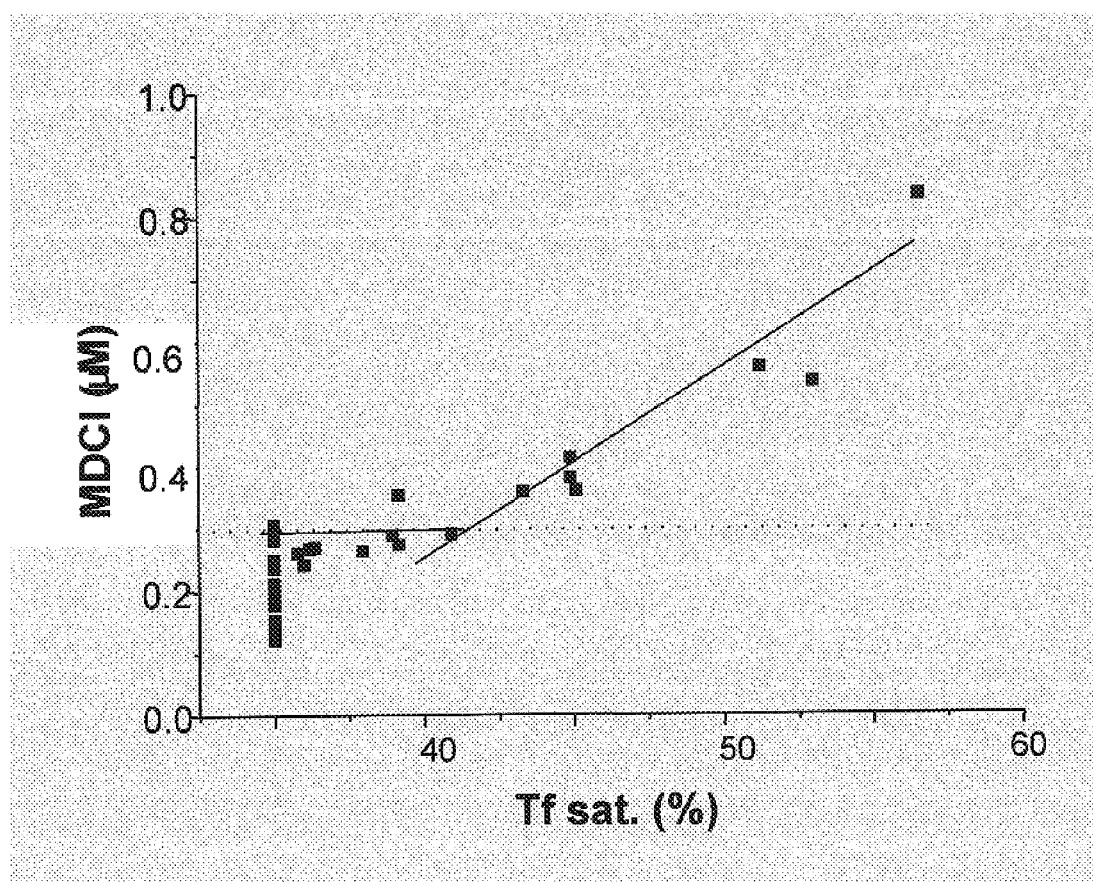

FIG. 13 is a graph illustrating a linear correlation between MDCI levels and transferrin saturation in iron-supplemented patients with end stage renal disease (ESRD) treated in the dialysis unit of Shaarc Zedek Medical Center (SZMC), Jerusalem, Israel.

Figure 14:
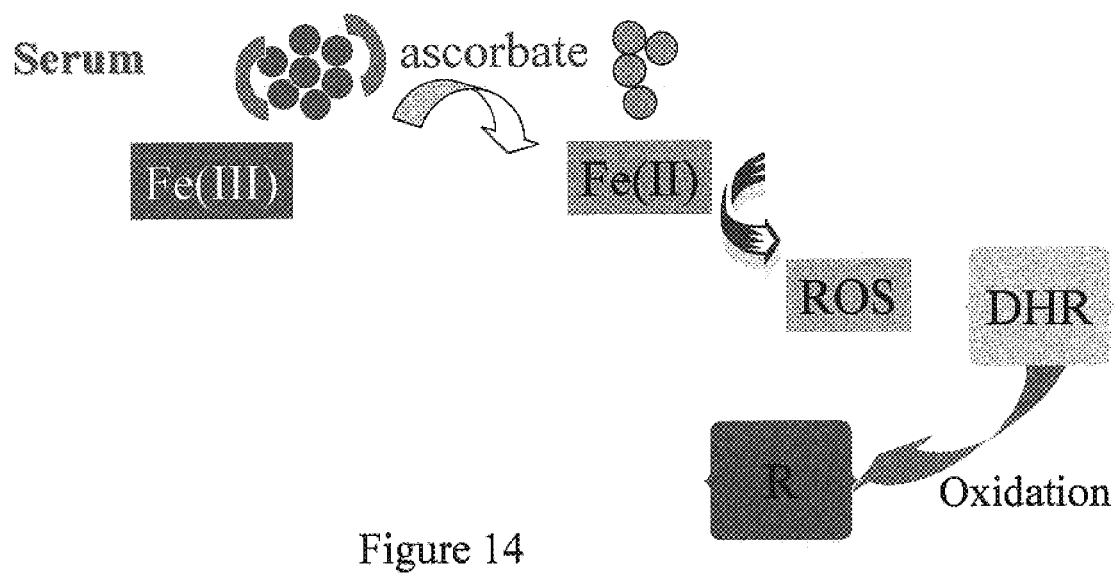

FIG. 14 is a schematic illustration of LPI detection. LPI represents labile plasma iron. LPI is detection is effected by reducing the iron with ascorbate, which in turn leads to the oxidation of dihydrorhodamine 123 (DHR) and its conversion into the fluorescent rhodamine (R).

Figure 15A:
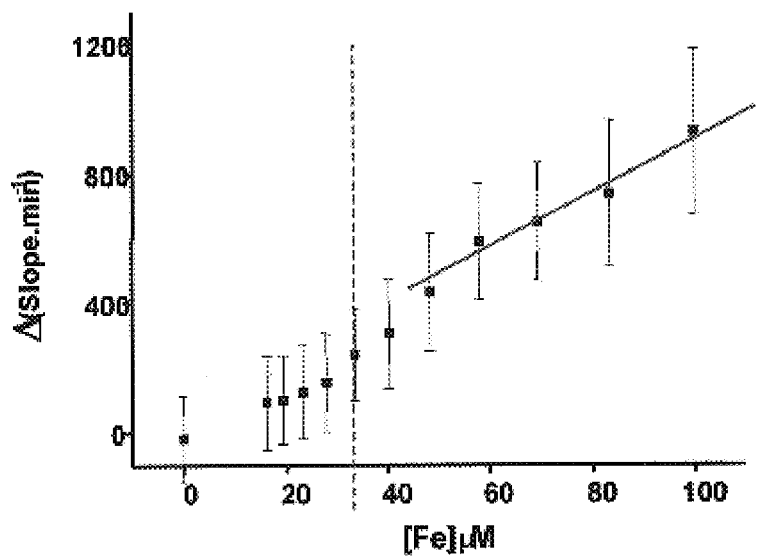
Figure 15B:
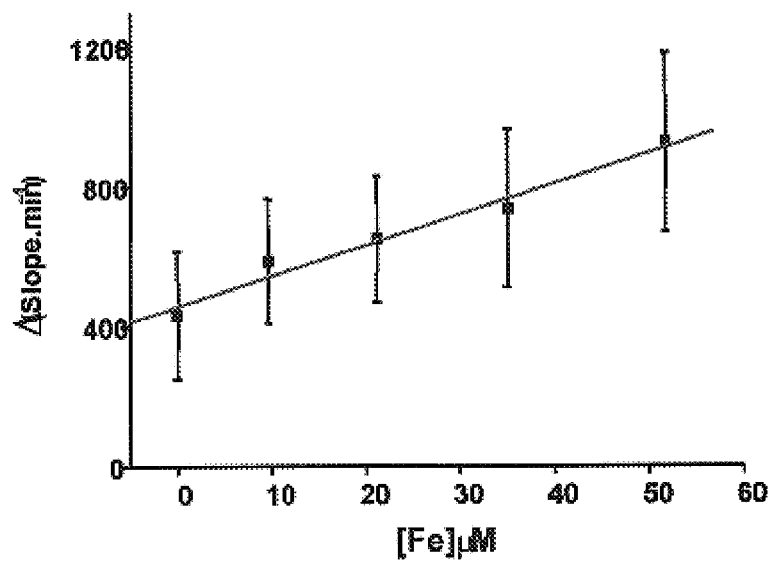

FIGS. 15A–B are calibration curves depicting time dependent fluorescence emission of serum samples (average of n=12±SE) supplemented with ascorbate and DHR, as a junction of input iron concentration. FIG. 15A depicts the full range of fluorescence values obtained with the indicated input iron concentration. The linear regression line applies to values of iron concentration beyond the fill saturation of transferrin binding sites present in the serum of each individual patient. FIG. 15B depicts the range of slopes (from FIG. 15A) of iron concentration added in excess to that required to fully saturating the serum transferrin, which for sera of HH patients is 50 µM.

Figure 16A:
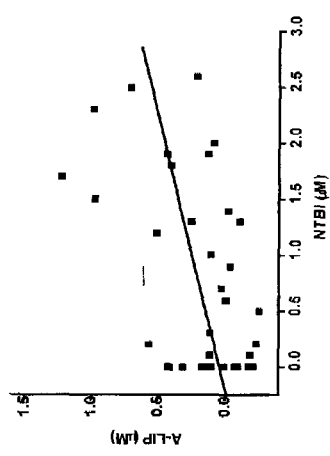
Figure 16B:
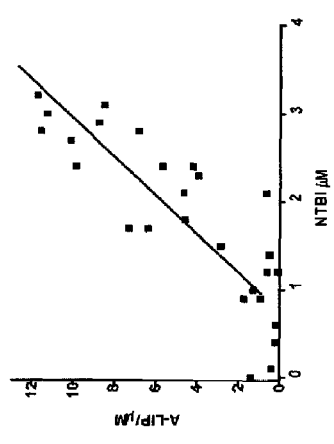
Figure 16C:
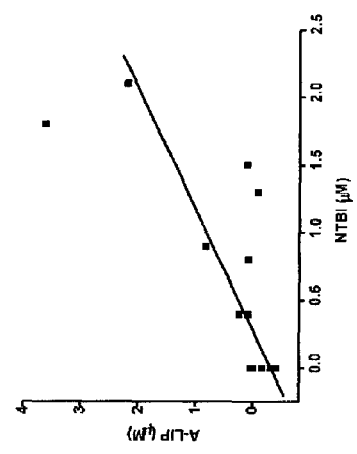

FIGS. 16A–C are graphs illustrating linear correlations between MDCI and LPI levels in a number of patient populations: FIG. 16A—HH patients; FIG. 16B—Thai Thalassemia patients; FIG. 16C—Israeli MDS patients.

DESCRIPTION OF THE PREFERRED EMBODIMENTS

The present invention is of novel molecules, which can be used to diagnose disorders associated with abnormal levels of free iron, such as hereditary hemochromatosis.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

The presence of non-transferrin-bound iron (NTBI) in the circulation is associated with iron-overload pathologies, typical of for example hemolytic patients and dialysis patients.

Thus, accurate assessment of NTBI concentration is critical in diagnosis and therapy of various pathologies. Early diagnosis of disorders associated with abnormal levels of free iron, is highly significant for disease management particularly in the asymptomatic stage. Additionally, efficacy of iron chelating drugs hinges on accurate NTBI quantification. Furthermore, cost-effective, non-invasive and accurate assessment of NTBI may provide a screening tool for populations at high-risk for Iron-overload.

Currently available methods of assessing NTBI concentrations include the use of low affinity iron chelators which are capable of complexing with low molecular weight iron followed by chromatography-based quantification of NTBI; methods which depend upon the catalytic activity of free iron such as by the catalytic generation of thiobarbituric acid reactive material generated by the action of free iron on bleomycin complexed with DNA, and a stepwise procedure which includes capturing free iron using a surface bound chelator and a second step of iron detection using a fluorescent marker.

In addition to being costly and cumbersome, these methods are limited by relatively low throughput efficiency. Additionally, currently available fluorescent markers are highly sensitive to environmental condition, which confound assay readout results. Moreover, all methods available to-date fail to consider both immobilized iron and endogenous apo-transferrin which is universally found in biological samples except in cases of extreme iron-overload, resulting in low estimation of in vivo NTBI levels.

As described hereinunder and in the Examples section which follows, the present invention provides molecules which can be utilized to detect NTBI in biological fluids even in cases in which NTBI is inaccessible for iron detection or when apo-transferrin is present in the tested sample.

Thus, according to one aspect of the present invention there is provided a molecule which is suitable for use as an indicator of free iron levels in a biological sample.

The phrase "biological sample refers to a biological fluid such as blood, serum, plasma, lymph, bile fluid, urine, saliva, sputum, synovial fluid, semen, tears, cerebrospinal fluid, bronchioalveolar large fluid, ascites fluid, pus and the like.

As used herein the phrase "free iron levels" refers to non-transferrin bound iron (i.e. NTBI).

As used herein the term "NTBI" refers to directly chelatable iron (DCI) which is accessible to exogenous iron chelators; mobilizer-dependent chelatable iron (MDCI) which is accessible to exogenous iron chelators upon addition of mobilizing agents; and labile plasma iron (LPI) including redox active iron, which redox activity is eliminated upon addition of exogenous iron chelators.

"Mobilizing agents" are capable of mobilizing immobilized iron which include any free iron, which generally circulates as low molecular weight complexes such as citrate, phosphate [Grootveld (1989(J. Biol. Chem. 264: 4417–4422)] and certain amino acids or in association with other serum proteins such as albumin. Or, microaggregates of iron, which occur due to very low solubility of $Fe^{+3}$ in physiological solutions resulting in polynuclear aggregates of iron.

The indicator molecule according to this aspect of the present invention includes an iron binding moiety and a signal generating moiety.

The phrase "iron binding moiety" refers to iron chelators, which bind to or combine with iron ions, including all synthetic and natural organic compounds known to bind iron, and any molecule of biological origin, or by-product or modified product of a molecule of biological origin, such as proteins, sugars or carbohydrates, lipids and nucleic acids, and any combination thereof, that may bind iron ions.

Examples of iron binding proteins include but are not limited to transferrin, apo-transferrin, lactoferrin, ovotransferrin, p97-melanotransferrin, ferritin, Ferric uptake repressor (FUR) proteins calcineurin, acid phosphatase, ferredoxin.

The use of transfer (Tf) as the iron binding moiety is preferable, since iron binding to Tf or apo-If is significantly faster than to other known iron binding molecules, which enhances the probability that free iron (including MDCI) will bind the indicator molecule rather tan to endogenous apo-Tf.

Chemical moieties which are suitable for use as the iron binding moiety of this aspect of the present invention include iron chelators. The phrase "an iron chelator" refers to a molecule comprising nonmetal atoms, two or more of which atoms are capable of linking or binding with a iron ion to form a heterocyclic ring including the metal ion.

Examples of iron chelators include but are not limited to desferrioxamine, phenanthroline, ethylene diamine tetraacetic acid (EDTA), diethylene triamine-pentaacetic acid (DTPA), N,N'-bis[2-hydroxybenzoyl]ethylene diamine-N, N'-diacetic acid (HBED) and the like. Other examples of iron chelators and related compounds are provided in U.S. Pat. Nos. 4,840,958, 5,480,894, 4,585,780, 5,925,318 and in Hider (1996) Acta Heamatologica 95:6–12.

The signal generating moiety of the indicator molecule described hereinabove, is selected such that the intensity of signal generated therefrom is related to the amount of the iron which is bound to the iron binding moiety. Preferably, the intensity of the signal is stoichiometrically related to the iron bound by the iron binding moiety.

One of the properties of ionic iron is its inherent ability to affect the fluorescence properties of fluorophores when in atomic or molecular contact, usually resulting in the quenching of the fluorescence signal, [Lakowicz, J-R. (1983) Principles of fluorescence spectroscopy, Plenum Press, New York, pp.266 ff.]. Hence, the signal generating moiety is preferably a fluorophore, which can be quantified via its fluorescence, which is generated upon the application of a suitable excitatory light. The use of a fluorophore as the signal generating moiety allows the generation of a direct correlation between changes in fluorescence and NTBI concentration.

A non limiting list of commercially available fluorophores suitable for use as the signal generating moiety of the present invention along with approximate absorption (Abs) and fluorescence emission (Em) is provided in Table 1 below. The listed fluorophores are available from Molecular Probes (www.molecularprobes.com).

TABLE I

| Fluorophore | Fluorescence color (Abs/Em) |
|---|---|
| Alexa Fluor 350 | Blue (346/442) |
| Marina Blue | Blue (365/460) |
| Pacific Blue | Blue (410/455) |
| Alexa Fluor 430 | Yellow-Green (433/539) |
| Fluorescein-EX | Green (494/518) |
| FITC | Green (494/518) |
| CALCEIN | Green (485/517) |
| Alexa Fluor 488 | Green (495/519) |
| Oregon Green 488 | Green (496/524) |
| Oregon Green 514 | Green (511/530) |
| Alexa-Fluor 532 | Yellow (532/554) |
| Alexa-Fluor 546 | Orange (556/573) |
| Tetramethylrhodamine | Red-Orange (555/580) |
| Rhodamine Red-X | Red-Orange (570/590) |
| Alexa Fluor 568 | Red-Orange (578/603) |
| Texas Red-X | Red (595/615) |
| Lucifer Yellow | 425/531 |
| BODIPY TMR | 544/570 |
| BODIPY 493/503 | 493/503 |
| BODIPY 499/508 | 499/508 |
| BODIPY 507/515 | 507/515 |
| NBD | 478/541 |
| Sulfonerhodamine | 555/580 |

Alternatively, a fluorophore can be a protein belonging to the green fluorescent protein family including but not limited to the green fluorescent protein, the yellow fluorescent protein, the cyan fluorescent protein and the red fluorescent protein as well as their enhanced derivatives.

Optionally, the signal generating moiety of the indicator molecule can be an enzyme which when in the presence of a suitable substrate generates chromogenic products. Such enzymes include but are not limited to alkaline phosphatase, β-galactosidase, β-D-glucoronidase (GUS) and the like.

It will be appreciated that a naturally occurring molecule such as an enzyme can comprise the indicator molecule of the present invention, wherein following iron binding a measurable conformational and/or a functional alteration is effected. For example, the aconitase enzyme is activated following iron binding [Klausner, R. D. et al., (1993) Cell 72:19–28].

According to a presently preferred embodiment of this aspect of the present invention the indicator molecule is fluoresceinated deferrioxamine (Fl-DFO, see FIGS. 1C–D).

According to presently another preferred embodiment of this aspect of the present invention the indicator molecule is 5-4,6-dichlorotriazinyl aminofluorescein (DCTF)-apo-transferrin i.e., Fl-aTf (see FIGS. 1A–B). The advantages of using this molecule in free iron detection are described hereinunder.

The indicator molecules of the present invention can be synthesized using well known chemical synthesis procedures. Detailed protocols describing how to use reactive fluorophores are available in www.molecularprobes.com.

For example, amine-reactive fluorophores (i.e., including a reactive group such as dichlorotriazinyl, isothiocyanate, succinimidyl ester, sulfonyl chloride and the like) can be used to modify proteins, peptides and synthetic oligonucleotides (see www.probes.com/media/pis/mp00143.pdf).

Amine-reactive fluorophores are mostly acylating reagents, which form carboxamides, sulfonamides, ureas or thioureas upon reaction with amines. It will be appreciated that the kinetics of the reaction depends on the reactivity and concentration of both the acylating reagent and the amine. It will be further appreciated that, buffers that contain free amines such as Tris and glycine must be avoided when using any amine-reactive probe. Ammonium sulfate used for protein precipitation must also be removed before performing such conjugations. In addition, high concentrations of nucleophilic thiols should be avoided because they may react with the reagent to form an unstable intermediate that could consume the fluorophore. Reagents for reductive alkylation of amines are also described in www.molecularprobes.com Chapter 2 and Chapter 3.

The most significant factors affecting an amine's reactivity are its class and its basicity. Virtually all proteins have lysine residues, and most have a free amine at the N-terminus. Aliphatic amines such as lysine's ε-amino group are moderately basic and reactive with most acylating reagents. However, the concentration of the free base form of aliphatic amines below pH 8 is very low; thus, the kinetics of acylation reactions of amines by isothiocyanates, succinimidyl esters and other reagents are strongly pH dependent A pH of 8.5 to 9.5 is usually optimal for modifying lysine residues. In contrast, the α-amino group at a protein's N-terminus usually has a $pK_a$ of ~7, so it can sometimes be selectively modified by reaction at near neutral pH. Furthermore, although amine acylation should usually be carried out above pH 8.5, the acylation reagents tend to degrade in the presence of water, with the rate increasing as the pH increases. Protein modification by succinimidyl esters can typically be done at pH 8.5, whereas isothiocyanates usually require a pH>9 for optimal conjugations; this high pH may be a factor when working with base-sensitive proteins.

Aromatic amines, which are uncommon in proteins, are very weak bases and thus unprotonated at pH 7. Modification of aromatic amines requires a highly reactive reagent, such as an isocyanate, isothiocyanate, sulfonyl chloride or acid halide, but can be done at any pH above ~4. A tyrosine residue can be selectively modified to form an o-aminotyrosine aromatic amine, which can then be reacted at a relatively low pH with certain amine-reactive fluorophores.

In aqueous solution, acylating reagents are virtually unreactive with the amide group of peptide bonds and the side chain amides of glutamine and asparagine residues, the guanidinium group of arginine, the imidazolium group of histidine and the nonbasic a cines, such as adenosine or guanosine.

Following conjugation, unconjugated fluorophore is removed, usually by gel filtration, dialysis, HPLC or a combination of these techniques. The presence of free fluorophore, particularly if it remains chemically reactive, can greatly complicate subsequent analysis with the indicator of the present invention.

Preferably, the indicator molecules of the present invention are characterized by a high fluorescence yield yet retain the critical parameters of the unlabeled iron binding moiety (i.e., iron binding).

It will be appreciated though, that oftentimes, highly labeled conjugates are likely to precipitate or bind nonspecifically. It may therefore be necessary to have a less-than-maximal fluorescence yield to preserve faction or binding specificity.

As described hereinabove, the indicator molecule of the present invention can be a chimeric protein including a protein fluorophore (e.g., GFP) linked to an iron binding protein. Such a chimeric protein can be produced via well known recombinant techniques.

Briefly, an expression construct (i.e., expression vector), which includes a polynucleotide encoding the chimeric protein of the present invention positioned under the transcriptional control of a regulatory element, such as a promoter, is introduced into host cells.

The "transformed" cells are cultured under suitable conditions, which allow the expression of the chimeric protein encoded by the polynucleotide.

Following a predetermined time period, the expressed fusion protein is recovered from the cell or cell culture, and purification is effected according to the end use of the recombinant polypeptide.

Depending on the host/vector system utilized, any of a number of suitable transcription and translation elements including constitutive and inducible promoters, transcription enhancer elements, transcription terminators, and the like, can be used in the expression vector [see, e.g., Bitter et al., (1987) Methods in Enzymol. 153:516–544].

Other then containing the necessary elements for the transcription and translation of the inserted coding sequence (encoding the chimera), the expression construct of the present invention ear also include sequences engineered to optimize stability, production, purification, yield or toxicity of the expressed fusion protein.

For example, a cleavable fusion protein can be engineered to include the indicator molecule of the present invention and a cleavable moiety. Such a fusion protein can be designed so that the chimeric protein can be readily isolated by affinity chromatography; e.g., by immobilization on a column specific for the cleavable moiety. Where a cleavage site is engineered between the chimera and the is cleavable moiety, the chimera can be released from the chromatographic column by treatment with an appropriate enzyme or agent that disrupts the cleavage site [e.g., see Booth et al, (1988) Immunol. Lett. 19:65–70; and Gardella et al, (1990) J. Biol. Chem. 265:15854–15859].

A variety of prokaryotic or eukaryotic cells can be used as host-expression systems to express the fusion protein coding sequence. These include, but are not limited to, microorganisms, such as bacteria transformed with a recombinant bacteriophage DNA, plasmid DNA or cosmid DNA expression vector containing the chimera coding sequence; yeast transformed with recombinant yeast expression vectors containing the chimera coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the chimera coding sequence. Mammalian expression systems can also be used to express the chimera of the present invention. Bacterial systems are preferably used to produce recombinant proteins since they enable a high production volume at low cost.

In bacterial Systems, a number of expression vectors can be advantageously selected depending upon the the intended for the chimera expressed. For example, when large quantities of chimeras are desired, vectors that direct the expression of high levels of the protein product, possibly as a fusion with a hydrophobic signal sequence, which directs the expressed product into the periplasm of the bacteria or the culture medium where the protein product is readily purified may be desired. Certain fusion protein engineered with a specific cleavage site to aid in recovery of the chimera may also be desirable. Such vectors adaptable to such manipulation include, but are not limited to, the pET series of *E. coli* expression vectors [Studier et al. (1990) Methods in Enzymol. 185:60–89).

Other expression systems such as insects and mammalian host cell systems, which are well known in the art can also be used by the present invention.

Mammalian expression vectors used for fusing heterologous proteins to the N-terminus or C-terminus of fluorescent proteins are available from BD BioSciences Clontech (www.bdbiosciences.com).

In any case, transformed cells are cultured under effective conditions, which allow for the expression of high amounts of recombinant polypeptide. Effective culture conditions include, but are not limited to, effective media, bioreactor, temperature, pH and oxygen conditions that permit protein production. An effective medium refers to any medium in which a cell is cultured to produce the recombinant chimera protein of the present invention. Such a medium typically includes an aqueous solution having assimilable carbon, nitrogen and phosphate sources, and appropriate salts, minerals, metals and other nutrients, such as vitamins. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art.

Depending on the vector and host system used for production, resultant proteins of the present invention may either remain within the recombinant cell, secreted into the fermentation medium, secreted into a space between two cellular membranes, such as the periplasmic space in *E. coli*; or retained on the outer surface of a cell or viral membrane.

Following a predetermined time in culture, recovery of the recombinant protein is effected. The phrase "recovering the recombinant protein" refers to collecting the whole fermentation medium containing the protein and need not imply additional steps of separation or purification. Proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization.

Chimeric proteins of the present invention are preferably retrieved in "substantially pure" form. As used herein, "substantially pure" refers to a purity that allows for the effective use of the protein in the diverse applications, described hereinabove.

It will be further appreciated that commercially available indicator molecules can also be used according to this aspect of the present invention. For example, fluorescent DFO (FL-DFO) and calcein are commercially available from Molecular Probes Inc.

The indicator molecules of the present invention can be widely used to directly and sensitively detect free iron levels in biological fluids.

Thus, according to another aspect of the present invention there is provided a method of quantifying free iron levels in a biological fluid.

The method includes several method steps, schematically illustrated in FIG. 2.

First, a sample of the biological fluid is contacted with the indicator molecule of the present invention. Contacting is effected under conditions suitable for binding of the iron-binding moiety of the indicator molecule to free iron. Suitable incubation conditions are provided in the materials and experimental methods paragraph of the examples section which follows.

It will be appreciated that fluorescence detection sensitivity is oftentimes compromised by background signals, which may originate from endogenous sample constituents or from unbound or nonspecifically indicator molecules (i.e., background fluorescence). To compensate for background fluorescence, parallel samples are preferably incubated with excess unlabeled indicator molecule, which scavenges all iron in the sample (also referred to as Reagent B, see FIG. 2).

The signal is then detected and quantified to determine the levels of free iron in the biological fluid of the subject.

Signal detection may be effected by any suitable instrumentation such as a fluorescent microscope or an ELISA reader.

The intensity of signal produced in any of the detection methods described hereinabove may be analyzed manually or using a computer program.

Any abnormality in the levels of free iron in the sample is indicative of the presence of a disorder in the subject.

In general, free iron quantification is preferably effected alongside a look-up table or a calibration curve so as to enable accurate iron determination (see Example 2 of the Examples section below for further detail).

Embodiments of the method of this aspect of the present invention include the use of iron mobilizing agents and removal of endogenous apo-transferrin from the sample, to accurately determine the levels of free iron in the sample.

As described hereinabove, free iron is often found in low molecular weight complexes such as with citrate and albumin. To accurately determine free iron levels, the fluid sample obtained from the subject is preferably treated with a mobilizing agent, described hereinabove, prior to contacting with the indicator molecule of the present invention. Examples of mobilizing agents include but are not limited to sodium-oxalate, nitrilotriaacetate, ascorbate and salicylate.

It will be appreciated that the mobilizing reagent employed must balance the ability to detect maximal free iron levels, without contributing to iron release from iron-containing transferrin in a given sample.

Preferably, 10 mM sodium oxalate is used as the mobilizing reagent according to this aspect of the present invention.

It will be appreciated, though, that other mobilizing agents or other combinations thereof can be used providing that they cause quenching of an indicator molecule of the present invention which is not quenched in the absence of a mobilizing reagent while causing no quenching of samples which contain no free iron such as normal serum samples or human transferrin saturated with various concentrations of iron.

Another embodiment of the method of this aspect of the present invention includes the exclusion of endogenous apo-transferrin and/or iron free transferrin from the sample prior to free iron determination.

Apo-transferrin is universally found in human sera, except in cases of extreme iron-overload where the transferrin is 100% iron-saturated. Therefore the detection of free iron may be tendered more difficult once the sample contains nearly normal levels of apo-Transferrin. The use of Fl-aTF as a probe equalizes the probability that the mobilized iron will bind to the indicator molecule or to endogenous apo-Transferrin in the sample.

Exclusion of endogenous apo-transferrin can be effected by incubating (i.e., pre-clearing) the sample with anti-apo-transferrin antibodies, such as solid phase coupled anti-transferrin antibodies available from Pharmacia, Uppsala and Bio-Rad Laboratories, Hercules, Calif. Additionally or alternatively anionic beads such as MacroPrep® High S support beads available from Bio-Rad Laboratories, Hercules, Calif. can be used to exclude apo-transferrin from the sample.

Preferably, exclusion of apo-transferrin is effected by co-incubating the sample with an apo-transferrin binding metal other than iron such as Gallium and Cobalt. These metals mimic iron and bind to the indicator molecule of the present invention, preventing their reaction with iron [Breuer and Cabantchik Analytical Biochemistry 299, 194–202 (2001)].

However, when using such metals, measures are taken not to use indicator molecules which are affected by such metals. Hence, a preferably used indicator molecule is Fl-aTf, described hereinabove, which is not affected by Gallium due to a biochemical mechanism which is yet to be determined. This apparent insensitivity to Gallium gives the Fl-aTf indicator an iron-binding advantage over the endogenous Apo-transferrin, overcoming most of its interference.

As described hereinabove NTBI also refers to labile plasma iron (LPI) including redox active iron, which redox activity is eliminated upon addition of exogenous iron chelators.

Redox active iron [i.e., ferrous iron] is highly damaging when labile [Herbert (1994) Stem Cells 92:1502–1509]. Ferric iron [i.e., e(III)] is a relatively nontoxic form of iron. However, ferrous iron [i.e., Fe(II)] plays a significant role in the generation of oxygen species (ROS), excess of which has been proven to be extremely harmful to the health of individuals. Free radical toxicity is produced primarily by the hydroxy radical (.OH). Most of the .OH generated in vivo comes from iron-dependent reduction of $H_2O_2$ [Halliwel (1986) Archi. Biochem. Biophys. 46:501–14]. It is well established that redox active iron and its reaction products (i.e., ROS) promote numerous diseases including cancer, diabetes, heart diseases and liver diseases [Halliwell, B. and Guterridge, J. M. (1995). Role of free radicals and catalytic metal ions in Human Disease: An overview. Meth. Enzymol 186:1–85].

Accordingly, it is essential to quantify redox active iron in a biological fluid.

Thus, according to yet another aspect of the present invention there is provided a method of quantifying redox active iron in a biological fluid.

The method includes several method steps, schematically illustrated in FIG. 14.

First, a sample of the biological fluid is contacted with a reducing agent. The reducing agent is selected capable of reducing free iron from ferric to ferrous form. Suitable reducing agents according to this aspect of the present invention include, but are not limited to, ascorbic acid, dithionite, mercaptoacetic acid, dithiothreitol.

Preferably, a physiological concentration of ascorbic acid is used according to this aspect of the present invention.

Reduced iron is capable of reacting with any oxygen species dissolved in the sample to generate redox active iron reaction products (e.g., ROS).

Reducer-treated sample is then contacted with a detector molecule, which can be measurably activated upon interaction with the newly generated redox active iron reaction product. The detection molecule is selected such that its activation is related to he amount of the redox active iron reaction products.

Finally, activation of the detection molecule is quantified, thereby quantifying redox active iron levels in the biological fluid.

Preferably, the detector molecule is a molecule which undergoes a spectrophotometric/fluorescence change following interaction with the redox active iron reaction products, such as ROS. Examples include but are not limited to dihydrorhodamine-123 (DHR), which converts to fluorescent rhodamine, dihydrofluorescein, which converts to fluorescein, dihydroresorufin which converts to resorufin and the like.

Quantification of detector molecule activation is effected according to the methodology described hereinabove.

It will be appreciated that to specifically identify redox active iron reaction products which are generated by the catalysis of iron alone, a parallel sample is subjected to the treatment described hereinabove and an excess of iron chelator (preferred concentration ranges are provided in the Examples section) Any increase in fluorescence reflects background ROS generation.

It will be appreciated that the indicator molecules of the present invention can be included in a diagnostic or therapeutic kit. For example, indicator sets including one or more of the following components described hereinabove (i.e., an indicator molecule, a mobilizing agent, manganate, a non-labeled iron chelator, an apo-transferrin binding metal other than iron, an anti-apo transferrin antibody, anionic beads), can be packaged in a one or more containers with appropriate buffers and preservatives and used for diagnosis or for directing therapeutic treatment.

The indicator molecules of the present invention can be widely used to directly and sensitively detect NTBI which persists in sera of patients, even with low transferrin saturation.

Thus, according to still another aspect of the present invention there is provided a method of determining presence or absence of a disorder associated with abnormal levels of free iron in a biological fluid of a subject.

Examples of disorders and conditions which are associated with abnormal levels of free iron include, but are not limited to, hemolytic diseases hemoglobinopathies, thalassemia, thalassemia major, anemia, sickle cell anemia, aplastic anemia, megaloblastic anemia, myelodyplasia, diseases which require repeated transfusions, diseases which require dialysis, hereditary hemachromatosis, cancer, heart diseases, Megaloblastic Dysplasia Syndrome (MDS) and rheumatoid arthritis.

Preferred individual subjects according to the present invention are mammals such as canines felines, ovines, porcines, equines, bovines, humans and the like.

Methods of obtaining body fluids from mammals are well known in the art. It will be appreciated that the source of the fluid varies between the different disorders identified.

Quantification of free iron levels is effected as described hereinabove.

Determining iron levels originating from a biological sample of a patient is preferably effected by comparison to a normal sample, which sample is characterized by normal levels of free iron (i.e., no detectable free iron).

The availability of an accurate and non-invasive free iron quantification method is also useful in disease management. The diagnostic method of the present invention, can aid a medical professional diagnosing of a patient even with low levels of free iron and instructing the patient on the type of diet to maintain in terms of iron content and iron availability for adsorption, which can result in iron overload.

Due to its large applicability the method of this aspect of the present invention can be easily implemented in large scale screening of populations for iron overload (see Examples 6–8 and 11 of the Examples section).

For example, the widespread use of a genotype assay that identifies the common C282Y mutation in the HFE gene has allowed an earlier diagnosis of hereditary hemochromatosis to be made in many subjects. However, this assay has recently been found to give a false-positive C282Y homozygous result in half of the subjects in one population screening study due to the presence of a single nucleotide polymorphism (SNP) that interfered with primer binding in the PCR assay. Thus, use of the HFE genotype assay as the sole diagnostic criterion for hereditary hemochromatosis is not recommended [Jeffery (2000) Genet. Test. 4:143–6]. Therefore the present methodology may be preferably used for large scale detection of free iron overload. Preferably, correlation of prior art methods for determining iron overload and the method of this aspect of the present invention is effected The indicator molecules of the present invention can also be utilized in an assay for uncovering potential regulators of free iron levels including intracellular iron and extracellular iron, such as for examples regulators of the HFE gene family [including HFE1—The HH gene; HFE2—Juvenile Hemochromatosis on human CHR 1, HFE3—mutations in TFR2 gene; HFE4—mutations in SLC11A3 (Ferroportin 1, IREG1 or MTP1, Genebank NM_014585) and HFE5—Human ferritin gene], mutagens, transferrin antagonists and the like [Cabantchik et al. (2002). In Templeton D. M. (2002) Molecular and cellular Iron transport Marcel Dekker, Inc. NY, pp. 539–558; Esposito et al Anal. Biochem. 304, 1–18 (2002)].

Thus, according to still another aspect of the present invention there is provided a method of identifying regulators of free iron levels.

The method of this aspect of the present invention is effected by exposing cells to a plurality of agents and determining which agent is capable of altering free iron levels as compared to untreated cells, thereby identifying a potential regulator of free iron levels.

Determining which agent is capable of altering free iron levels is accomplished by a free iron quantification methodology effected according to the teachings of the present invention, described hereinabove.

It will be appreciated that the method according to this aspect of the present invention is capable of identifying agents which alter extracellular and/or intracellular free iron levels. Free iron is found in the cytosol of mammalian cells, at levels ranging from 0.1 to 1 μM (Esposito et al Analytical Biochemistry 304, 1–18 (2002)). Detection of intracellular free iron [i.e., plasma labile iron pool (LIP)] can be effected by any of the detector molecules described hereinabove. Preferably used are detector molecules which exhibit enhanced cellular up-take and intracellular retention such as. For example, calcein and fluorescein-labeled phenanthroline [Cabantchik et al. (2002). In Templeton D. M. (2002) Molecular and cellular Iron transport. Marcel Dekker, Inc. NY, Esposito et al Anal. Biochem. 304, 1–18 (2002)].

Putative agents, which can be utilized according to the present invention include, can include small molecules, such as, for example, naturally occurring compounds (e.g., compounds derived from plant extracts, microbial broths, and the like) or synthetic organic or organometallic compounds; the agents of the present invention can also include viruses and microorganisms such as bacteria and intracellular parasites.

Various growth conditions can also be used as putative agents. Conditions suitable for use as putative agents according to the present invention include, but are not limited to, temperature, humidity, atmospheric pressure, gas concentrations, growth media, contact surfaces, radiation exposure (such as, gamma radiation, UV radiation, X-radiation) and the presence or absence of other cells in a culture.

Various cell types can be used by the present agent screening methodology. Preferably used are cells which elicit high extracellular free iron levels. The use of such cells allows for a straightforward identification of agents which cause down-regulation of free iron levels, such agents are considered as putative drugs against disorders associated with iron overload. Examples of such cells include but are not limited to in-vitro established mononuclear cell lines and primary cultures (both in semi solid and liquid media) of erythroid progenitor cells obtained from thalassemic patients [Fibach (2001) Semin. Hematol. 38(4):374–81; Kriakou et al. (1998) Eur. J. Haematol. 60:21–7], human U937 cell-line, human K562 cell-line, human HcpG2 cell-line, Rat hepatocytes, MEL cell-line, ratv P19 neuronal differentiated cells, rat cardiomyocytes, mouse J774 cell-line, CaCo2 human colon epithelial cells, human lymphocytes isolated from patients.

The method of this aspect of the present invention determines changes in free iron levels, as indicator of a free iron regulator. To this end measures are taken to maintain cell viability following exposure to the putative agents, such that metabolic activity is retained.

This screen allows to find, test and develop novel drugs effective for clinical use in patients which are prone to cellular damage triggered by iron over-load.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M, ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1–4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I–III Cellis, J. E., ed. (1994); "Current Protocols in Immunology" Volumes I–III Coligan J. E., ed. (1994); Stites et al. (eds), "Basic and Clinical Immunology" (8th Edition)) Appleton & Lange, Norwalk, Conn. (1994); Mishell and Shiigi (eds), "Selected Methods in Cellular Immunology", W. H. Freeman and Co., New York (1980), available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1–317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

EXAMPLES

Materials and Experimental Methods

Chemicals—Reagent A was prepared by mixing 2.5 µM Fluorescein-DFO (Fl-DFO (Molecular Probes, Eugene, Oreg.) with Fe-free HBS buffer including 150 mM NaCl and 20 mM Hepes, pH 7.3. Reagent B was prepared similarly to Reagent A but included 0.5 mM DFO (Novartis, Basel, Switzerland), as well.

Preparation of fluorescein-conjugated apo-Transferrin (Fl-aTF) and iron depleted Transferrin (FL-TF)—100 µM 5-(4,6-dichlorotriazinyl) aminofluorescein (DCTAF, Molecular Probes, Eugene, Oreg.) from a freshly prepared 10 mM solution in dimethylsulfoxide was added to a solution containing 8 mg/ml apo-Transferrin (Kamada, Kibbutz Kama, Israel) (100 µM, based on a, MW of 80 kD) in 100 mM NaHCO$_3$, pH 8.4. Following a 30 minute incubation at 37° C. in the dark, 5 mM L-lysine was added from a solution containing 0.5 M L-lysine, pH 8, in order to terminate the coupling reaction. The product Fl-aTF was extensively dialyzed against HBS, divided into aliquots and stored frozen at −20° C. The final preparation yielded a single fluorescent band of approximately 80 kD in polyacrylamide electrophoresis determinations. The fluoroscein concentration in Fl-aTF was determined to be 84 µM by measuring absorbance at 496 nm, using DCTAF as standard solution, giving a ratio of aTf: fluoroscein of 1:0.84. Comparison of the Iron-induced quenching of Fl-aTF from three separate preparations showed them to be virtually identical.

FL-TF was prepared in an identical manner as FL-aTF, with the difference that iron-saturated human transferrin (from Kamada, Kibbutz Kama, Israel) was used instead of iron-free transferrin for reaction with DCTAF. The FL-TF was rendered iron-free by exhaustive dialysis against 37.5 mM Na-Citrate, pH 5.0, and then the citrate was removed from the preparation by exhaustive dialysis against HBS.

Preparation of samples with known Iron concentrations—100 µl of 70 mM nitrilotriacetate (NTA, Sigma, St. Louis, Mo.) (in its sodium form) at pH 7.0 was added to 100 µl of 10 mM ferrous (Fe) ammonium sulfate in double distilled water in a polyethylene tube, to produce an Fe:NTA (5:35 mM) complex.

Serial dilutions of Fe:NTA complexes were performed in Iron-free Hepes buffered solution (HBS) containing 150 mM sodium chloride and 20 mM commercially available Hepes buffer, pH of 7.3. A maximum of 12 incremental dilutions was performed, resulting in Iron concentrations ranging from 200 to 0.2 µM.

Assaying the samples—20 µl of each iron dilution was transferred in quadruplicate to 96-well flat-bottom polystyrene plates (Nunc, Roskilde, DK) and 100 µl reagent A (i.e., fluorescent iron chelator) or reagent B (i.e., a mixture of a fluorescent iron chelator with excess non-labeled iron chelator) were added. Samples were incubated in the dark for 1 hour at room temperature. Fluorescence was determined using a multiwell plate reader (BMG LabTechnologies, Offenburg, Germany) with excitation/emission filters of 485/538 nm. The ratio of fluorescence obtained for samples treated with reagent A versus reagent B was plotted as a function of Iron (Fe) concentration.

MDCI assay reagents: Reagent A consisted of HBS (150 mM sodium chloride, 20 mM Hepes, pH 7.3) containing 10 mM sodium oxalate (from Analar, Poole, UK), 0.1 mM GaCl$_3$ (from Aldrich Chem. Co., Milwaukee, Wis.), and 0.6 µM (0.05 mg/ml) Fl-aTF. Reagent B consisted of the same materials as Reagent A, with the addition of a 40-fold excess of apo-Transferrin, at a concentration of 2 mg/ml. Both reagents were stored frozen at −20° C. in aliquots and thawed just prior to use.

Assay for determining MDCI levels: Samples of 10 µl of serum (defiled as "input samples") containing unknown quantities of MDCI or Iron-free HBS (serving as the assay blank) were placed in quadruplicates in 96-well flat-bottom polystyrene plates. 200 µl of Reagent A or 200 µl of reagent B was each added to two of the four wells, respectively. The plates were incubated in the dark for one hour at room temperature. Fluorescence determination and calculation of MDCI concentration were conducted as described hereinabove.

Construction of a calibration curve for Iron (DCI) concentration determination: DCI concentrations may be estimated by the generation of a calibration curve. Known quantities of free iron (i.e., NTBI) are subjected to the assay system of the present invention (described in Example 1) adopted to include FL-DFO as the DCI probe, and resulting fluorescent values obtained are plotted as a function of iron concentration. Thus fluorescent values obtained from unknown concentrations in biological samples can be used to obtain actual concentrations, based on the calibration curve.

Assay for determining LPI levels—Duplicate samples of 20 µl of serum were treated with 180 µl of a reaction mixture including ascorbic acid (Sigma, St. Louis, Mo.) 40 mM final; Dihydrorhodamine 123, dihydrochloride salt ("DHR", Biotium, Hayward, Calif.) 50 µM final, in iron-free HBS at 37° C. An additional set of 20 µl duplicates were treated with the same solution as above, but containing the iron chelator L1 (deferiprone, Apotex, Canada) 50 µM. Fluorescence was measured along a duration of 40 min at 37° C. (slopes of change in fluorescence over time were calculated from 15' to 40'). The differences of slopes (plus/minus L1) for each sample were then converted into values of LPI in µM using a calibration curve such as described in FIG. 15.

Construction of a calibration curve for LPI concentration determination—20 µl of serum were treated with 80 µl of Fe:NTA (as hereinabove) diluted in HBS containing 10 mM Sodium Bicarbonate for 30 minutes at 37° C. Iron concentrations in the serum sample ranged from 0 to 100 µM. Samples of 20 µl of the iron-treated serum were then subjected to the LPI assay as described under "Description of the method and materials for LPI detection assay". In order to correct for the initial 5-fold dilution of the serum samples, the slopes of the calibration curve were multiplied by a factor of 5.

Example 1

An Assay System to Detect NTBI as DCI and MDCI

Fundamental problems in the accurate measurement of non-transferrin-bound iron (NTBI) using current methodology include the complexity, poor efficiency and hence high cost of the assay systems currently in use. Because current detection methods for non-transferrin-bound iron (NTBI) are sub-optimal, it was essential to design a more accurate assay system, with higher throughput efficiency and greater applicability in clinical settings.

While reducing the present invention to practice, a novel assay which depends on the construction of a metalosensor for detecting iron was developed. The metalosensor or iron detector is based on an iron binding moiety (i.e., iron chelating moiety, CH) and a signal generating moiety (i.e., reporter group, F) that senses the chelator-bound iron (see FIGS. 1A–D). The basic feature of the method is that the binding of the metal to the CH, and hence the change in the spectroscopic properties of F, are stoichiometric (see FIGS. 1A–D). A schematic depiction of one example of the method of the present invention illustrating features of the novel, sensitive yet remarkably simple assay system to detect NTBI is provided in FIG. 2.

The assay system is capable of detecting all forms of NTBI including directly chelatable iron (DCI) and mobilizing dependent chelatable iron (MDCI).

In the assay system, a biological sample (FIG. 2, normal serum, or serum with DCI/MDCI) is reacted with a solution containing a fluorescent-labeled chelator (Fl-CH, referred to as "reagent A"). Following the addition of the fluorescent-labeled chelator, fluorescence is determined via fluorometry. Since free Iron is capable of quenching fluorescence when in proximity to the metal, samples containing NTBI produce a detectable decrease in fluorescence (FIG. 1E and FIG. 2, low fluorescence). The magnitude of quenching is proportional to NTBI-chelator binding. Thus, changes in fluorescence indicate proportional changes in NTBI concentration.

To preclude the possibility of quenching or interference due to other factors in the sample (i.e., non-specific interference with fluorescence), a duplicate sample is assayed using the fluorescent-labeled Iron chelator (FIG. 2, Reagent A) combined with a large excess of un-labeled chelator, (FIG. 2, "Reagent B"). Thus, the excess chelator serves to neutralize NTBI's ability to quench the fluorescence of the probe. A decrease in fluorescence of the sample treated with reagent B is regarded as background quenching, and not a reflection of NTBI concentration in the sample. NTBI concentration in a given biological sample is expressed as the ratio NTBI-mediated (Reagent A) fluorescence and background (Reagent B) fluorescence.

Where the biological sample in question contains all its iron bound by transferrin (i.e., normal serum, FIG. 2), and no Iron is available for binding to the chelator, measurement of fluorescence in reagent A will be high and roughly equal for both NTBI-mediated and background measurements (FIG. 2, reagents A and B), without interference from background quenching by elements within the biological sample.

Thus, the combination described herein, of chelators and a binding-sensitive fluorescent signal generator provide a novel, sensitive high throughput assay system to detect and quantify NTBI.

Example 2

Determination of DCI (Directly-Chelatable Iron) in Serum with FL-DFO

In order to demonstrate the versatility of the assay of the present invention, the fluorescent chelator FL-DFO, an analogue of DFO, was used to determine the directly chelatable iron (i.e., concentration of iron that is directly accessible to an iron chelator in a body fluid, DCI). The method is essentially as described for Example 1 hereinabove, and depicted schematically in FIG. 3. Note that with the designated assay conditions, no iron is chelated by FL-DFO from Tf (FIG. 3) In this DCI assay there are no agents added for mobilizing NTBI or for blocking apo-Tf in the serum sample, since Tf is mostly iron-saturated.

In order to determine assay sensitivity and provide a reference curve for the extrapolation of test results, the assay described in Example 1 was conducted on serial dilutions of known concentrations of Iron (FIG. 4).

Calibration curve generated showed fluorescence plateaus at an Iron concentration of 12.5 µM, indicating saturation of the Fl-DFO (final concentrations of Fe and Fl-DFO were each approximately 2.1 µM). This 1:1 quenching ratio matched the predicted stoichiometry for Fl-DFO:Fe, each DFO molecule binding one Fe molecule, confirming the direct correlation between the changes in fluorescence and Iron concentration.

The region of the plot most linear and therefore most useful for calculating NTBI concentration corresponded to Iron concentrations of 0–6.25 µM in the input sample (FIG. 4). The upper and lower limits of detection were therefore roughly 7 and 0.4 µM, respectively.

DCI levels detected in 48 serum samples (i.e., control sera) were calculated using the calibration curve. Values obtained showed that serum samples from normal subjects contained no detectable DCI levels i.e., DCI<0.3 µM, which is within the error margin of the assay.

Thus the method of the present invention effectively, accurately and reproducibly detects free Iron in solution in a range of concentration of roughly 0.4–7.0 µM.

Example 3

Clinical Applications of DCI Assay

In order to determine the clinical applicability of the DCI assay, chelator binding of iron from human serum samples was assayed with samples representing a variety of iron-binding pathologies, treatment protocols and assay conditions.

Assay of Desferrioxamine-chelatable Iron in Normal and Iron-Overloaded Serum—The application of the DCI assay to populations of patients with various chronic diseases of iron overload is given in Table 2, below.

TABLE 2

| Group | Total Number | DCI (+) Samples (%) | Average of DCI (+) (µM) | Range of DCI (+) (µM) |
|---|---|---|---|---|
| Thalassemia major (TL)* | 16 | 91 | 4.9 | 1.7–8.6 |
| Thalassemia major (IL)* | 11 | 69 | 5.3 | 1.5–6.9 |
| HHC (Portugal)§ | 30 | 9 | 0.6 | 0.4–1.1 |
| HHC (NL) | 9 | 0 | — | — |
| Controls§§ | 48 | 0 | — | — |

Table 2 legend - TL-Thailand; IL-Israel; NL-Netherlands; HHC-hereditary Hemachromatosis;
* - Sera from transfusional iron overload - predominantly β-thalassemic children in Israel and non-transfusion dependent β-EHb (variant hemoglobin E) adults in Thailand;
§ - Sera from Portuguese patients of Oporto area sampled over a period of several months. 1–5 samples were obtained from each patient with a total of 86 samples during a period of venesection treatment. Calculation of % DCI positive samples (+) was done on a pool of total results;
§§ - Randomly selected serum samples from non-iron-overloaded individuals. All values <0.3 µM were considered negative.

The serum samples were assayed as describe hereinabove (Example 2), and DCI values determined from the standard calibration curve (FIG. 4). Note that the DCI in sera from patients with known, hereditary and chronic iron-related blood disorders (Thalassemia Major and Hemochromatosis) is representative of clinical condition: Thalassemia and untreated Hemochromatosis patients have consistently elevated DCI levels, whereas treated (Table I, IIIC NL) Hemochromatosis patients have reduced DCI values, in the normal range. Thus, the DCI assay provides a sensitive and accurate assessment of the state of iron overload in human sera Example 4

Assay of Desferrioxamine-chelatable Iron in Chelation Therapy

By selecting fluorescent-conjugated chelators with desired iron-binding characteristics, the methods of the present invention can provide sensitive assessment of iron bound to chelators used in clinical chelation therapy protocols. One such application was tested with patients receiving the oral chelator L1 (deferriprone). A schematic representation of the assay shows how iron mobilized from the tissues and delivered to the plasma in the form of L1-bound iron can be analyzed in plasma or sera by the DCI method, using Fl-DFO or Fl-aTF (FIG. 5).

When assessed under actual clinical conditions, with serum samples from Thalassemia patients (each patient is represented by a line in the graph) undergoing L1-chelation therapy in Thailand (FIG. 6A) and Israel (FIG. 6B), the methods of the present invention accurately reflected the L1-bound iron in the patient's plasma. DCI was detected in the samples assayed as described hereinabove (Example 2), and DCI values determined from the standard calibration curve (FIG. 4). Note that the increases in DCI detected reflect the tine course of oral L1 effectiveness in mobilizing iron into the blood. Thus, by selecting a suitable chelating element the DCI methods of the present invention can be used to assess on-line the efficacy of iron mobilization from tissue by chelation treatment.

Example 5

Accurate Determination of Mobilized Directly Chelatable Iron (MDCI) in Serum

Mobilized Directly Chelatable Iron (MDCI) is a subfraction of NTBI, which is associated with non-transferrin carriers in the blood (such as albumin, etc), whose detection is important for clinical analysis of iron metabolism. Detection of MDCI, using the fluorescent conjugated chelator of the present invention is schematically illustrated in FIG. 7. The assay for MDCI incorporates the basic features of the assay for DCI (illustrated in FIG. 2) except that reagents A and B are supplemented with iron mobilizing agents (e.g. oxalic acid, salicylic acid, citrate, nitrilotriacetate or ascorbate), singly or in combination. In one example the mobilizing reagent was oxalate, and Gallium chloride was added in order to prevent the mobilized iron from being transferred to serum aTf or partially iron-saturated Tf.

Unique features of the iron sensor Fl-aTF make it particularly suitable for the MDCI assay—Fluorescein-transferrin can be prepared under a variety of conditions, which will determine its properties as an iron sensor. In FIG. 8, two different preparations of fluorescein-apo-transferrin (Fl-aTF and Fl-TF) were compared with respect to their ability to bind iron in the presence and absence of the iron mobilizer oxalate and apo Tf-1 blocker Gallium (Ga). Conjugation of fluorescein to transferrin is described in detail in the Materials and Experimental section hereinabove. Briefly, FL-TF (FIG. 8A), was obtained by attaching fluorescein to iron-saturated Tf, followed by removal of the iron generate the iron-binding, apo-transferrin form. Fl-aTf (FIG. 8B) was obtained by attaching fluorescein to Iron-free apoTf. When tested for binding of iron (quenching of fluorescence) in the presence and absence of 10 mM oxalate (FIGS. 8A and 8B, open circles) and oxalate and 10 mM gallium (FIGS. 8A and 8B, open triangles), compared to no additions (FIGS. 8A and 8B, open squares), the inhibition of Fl-TF fluorescence quenching by gallium was clearly observed (FIG. 8A), while FL-aTF was strongly quenched by low concentrations of iron in the presence of gallium (FIG. 8B). Thus, FL-aTF retains its sensitivity to iron in the presence of oxalate-Gallium, and therefore can be used in the MDCI assay, whereas FL-TF, which is similar to conventional and commercially available preparations of fluoresceinated Transferrin, is not suitable for MDCI assay.

Calibration of MCDI assay with FL-TF and Measurement of MDCI in Human Serum Samples: FIGS. 9A and 9B demonstrate the calibration, and linear relationship, respectively, of available iron in the sample, and quenching of the FL-aTF fluorescence, expressed as a ratio of fluorescence using Reagent A and Reagent B (see Example 1, FIG. 2).

As in Example 2 (FIG. 4), available iron concentration was obtained via extrapolation of fluorescence measurements (ratio of fluorescence obtained with Reagents A and B) from the reference calibration curve. FIG. 9A shows the full range of iron concentrations tested (up to 25 µM). The most linear region of the calibration curve is shown in detail in FIG. 9B and corresponds to an Iron concentration range between 0–3.2 µM.

The MDCI assay was tested for it's applicability and reproducibility using human serum samples. FIG. 9B also shows that serum samples from normal individuals have no detectable DCI levels, i.e., the values obtained with 52 samples from normal individuals (FIG. 9B, "52 control samples") (represented an average ±S.D. for sera of 52 individuals without iron-overload) were <0.5 µM MDCI, which is within the margin of error of the assay. All serum samples with values below the designated "Arbitrary 0 value" (dotted line) were considered MDCI-positive. (Error bars indicate S.D., n=3). Thus, the MCDI assay of the present invention, using FL-aTF, can be applied to measurement of available iron in serum and plasma samples.

Example 6

Clinical Application of MDCI Assay

Assessment of available iron, as MDCI and NTBI, is of great clinical significance. Following are some statistics concerning the abundance of MDCI positive patient groupings.

Thalassemia—about 200,000 chronic patients worldwide; virtually all of the patients will have NTBI if not treated, roughly 50% will have MDCI despite treatment.

Hereditary Hemochromatosis (HH)—estimates of up to 1.5 million carriers of the HH mutation in USA and Europe, however not all carriers will develop symptoms of the disease. The majority of diagnosed patients will have MDCI unless treated, and roughly 20% will have MDCI despite treatment.

Iron supplemented individuals—including dialysis patients, iron-supplemented patients number about 300,000 chronic patients worldwide, and more than 2 million Megaloblastic Dysplasia Syndrome (MDS) patients world wide who undergo either periodic blood transfusions, EPO-iron (i.e., erythropoietin+iron) or iron maintenance treatments.

As shown in FIG. 10, virtually all patients (>90%) with Thalassemia will have MDCI if not treated with chelators. In Thai patients, who do not have access to iron chelators, the levels can reach the dangerous level of 15 µM MDCI. Among patients who are treated with chelators roughly 50% will show MDCI, depending on the frequency and type of treatment. Hereditary Hemochromatosis (HH) patients show fluctuating levels of MDCI, ranging from undetectable levels to 3 µM. Up to 75% of the patients will show MDCI at some point in time. Iron-supplemented individuals, such as dialysis patients who receive intravenous iron, have above-normal frequency of MDCI, up to 15%, ranging from undetectable levels to 2.5 µM. It will be appreciated that large population screening studies for NTBI are currently not available, however among randomly selected individuals up to 5% have been shown to be MDCI positive.

These conclusions apply also to MDS patients, which can benefit significantly from NTBI tests assessing their iron status and suggests a beneficial effects of oral-iron chelation therapy Assay of MDCI is indicative of NTBI status in Hereditary Hemochromatosis: In order to evaluate the efficacy of the novel methods of the present invention for assessing NTBI in predisposed individuals, MCDI levels were assayed in serum from Hereditary Hemochromatosis patients, prior to and following phlebotomy treatment A group of 80 HH patients was followed during a course of phlebotomy treatment over a number of months and their levels of transferrin saturation (determined by standard procedure) and MDCI (as detailed hereinabove) were determined periodically. The grouped results are shown in FIG. 11. MDCI is not detectable at Transferrin saturations of less than 35% (FIG. 11, open diamonds) and increases at Transferrin saturations above 35% (FIG. 11, closed squares). It will be appreciated that transferrin saturation is an established parameter of iron status, however it is known to fluctuate significantly (Dale J C, Burritt M F, Zinsmeister A R. Diurnal variation of serum iron, iron-binding capacity, transferrin saturation, and ferritin levels. Am J Clin Pathol. (2002); 117:802–8.). Therefore Transferrin saturation on its own is not a definitive indicator of iron status and the acceptable upper limit for "normal" Transferrin saturation is in many cases a matter of interpretation. In light of the present results, the methodology of the present invention provides an accurate measure for MDCI and as such is a valuable prognostic and diagnostic tool for NTBI-associated conditions.

Example 7

MDCI (NTBI) Levels are Reflect Clinical Status in Hemochromatosis Patient Prior to and Following Treatment A group of 14 HH patients under treatment at the Department of Transfusion Medicine, NIH, Bethesda Md., were treated by frequent phlebotomies (i.e., blood removal to deplete iron) until reaching a point of "Iron Depletion" at which iron status parameters, such as MCV (Mean Corpuscular Volume), Transferrin saturation and MDCI reached normal levels. Following Iron Depletion, the patients were phlebotomized only once every 12 weeks, a standard frequency for iron donations.

MCDI assay of samples from these patients, before and after phlebotomy (FIG. 12, closed diamonds), clearly indicates the variability of NTBI levels following phlebotomy. As can be seen from FIG. 12, the effect of the iron depletion treatment was already weakening in 8 of the patients, as detected by MDCI assay.

These results substantiate the importance of following MDCI (NTBI) levels in HH patients as a guide to determining the need for and frequency of phlebotomy treatment.

Example 8

Correlation Between MDCI Levels and Transferrin Saturation in ESRD Patients

A group of 40 ESRD patients from Shaare Zedek Medical Center (SZMC) undergoing regular hemodialysis and receiving intravenous iron supplements, was tested for transferrin saturation (determined according to standard clinical laboratory procedures) and MDCI one week following iron administration. As shown in FIG. 13, MDCI levels were not detectable at Transferrin saturation of less than 42% and increased proportionately as Transferrin saturation exceeded 42%.

Example 9

An Assay System to Measure the Redox Reactive Potential of Iron in Plasma or Serum: LPI (Labile Plasma Iron)

In addition to being a diagnostic indicator of iron overload, NTBI also entails a clinical hazard due to the potentially labile and reactive nature of this form of iron It is well established that iron in its reduced form, Fe(II), can reduce various forms of oxygen species (i.e., dioxygen or hydrogen peroxide) to give rise to highly reactive oxygen radicals with capacity for creating molecular damage. While iron that is bound to transferrin is protected from such reactions, NTBI and its sub-fractions DCI and MDCI are not, and therefore they are potential catalysts for the generation of reactive oxygen radicals (ROS).

Described below is a novel approach for estimating the capacity of plasma or serum iron for catalyzing the generation of reactive radicals. This fraction of reactive iron, which in the plasma is referred to labile plasma iron, hereinafter, LPI, appears in conjunction with NTBI probably deriving from NTBI.

The novel methodology for assessing LPI levels in biological fluids (e.g., plasma, serum) depends on reacting a biological sample with an agent capable of reducing NTBI from its Fe(III) form to its Fe(II) form. Reduced iron is then free to react with any oxygen species dissolved in the solution to generate ROS. The latter can be detected by any detector molecule that undergoes a spectrophotometric/fluorescence change after being acted upon by ROS, such as dihydrorhodamine-123 (DHR). FIG. 14 is a schematic illustration of the detection of LPI. LPI is revealed by reducing iron with ascorbate which in turn leads to the oxidation of dihydrorhodamine (DHR) and its conversion into the fluorescent rhodamine (R.).

To identify specifically the ROS that are generated via catalysis of iron alone and not due to other factors in the sample, each sample is subjected to two separate determinations using two reagents. In the first determination the sample is reacted with ascorbate and the ROS detector DHR (reagent 1) and in the second determination it is subjected Reagent 1 and a large excess of an iron chelator, (the combination hereinafter referred to as "Reagent 2"). Under these conditions, the excess chelator serves to neutralize LPI's ability to catalyze ROS production. Any increase in the fluorescence of the sample treated with reagent 2 is a reflection of background ROS generation, and not a reflection of LPI concentration in the sample. Thus, by obtaining the two measurements, and determining the ratio in their values, an LPI-mediated increase in fluorescence value can be obtained, serving as an indicator of LPI concentration, in a given biological sample.

In the occurrence that the biological sample in question contains all its Iron bound by transferrin (i.e., normal serum), hence no Iron is free for ROS generation, then measurement of fluorescence in reagents 1 and 2 will be roughly equal and will not be a reflection of other ROS-generating elements within the biological sample.

Example 10

Calibration of LPI

FIG. 15A is an example of a calibration curve, plotting the slope of time dependent fluorescence emitted from serum samples (average of n=12±SE) supplemented with ascorbate and DHR, as a function of the value of the input Iron concentration. The full range of values for the indicated input iron concentration is shown in FIG. 15A. The linear regression line applied to values of Iron concentration beyond the full saturation of transferrin binding sites present in the serum of each individual patient. FIG. 15B depicts the range of slopes (from FIG. 15A) for the iron concentration added in excess to that required to frilly saturate the serum transferrin, which for sera of HH patients was approximately 50 µM.

Example 11

LPI Levels in Different Patent Groups and its Correlation with MDCI

FIGS. 16A–C illustrate linear correlations between NTBI (measured here as MDCI) and LPI levels in three different patient populations: FIG. 16A for HH patients (35 samples), FIG. 16B for Thalassemia patients from Thailand (35 samples) and FIG. 16C for Megaloblastic Dysplasia Syndrome (MDS) patients from Israel, further described hereinunder. The graphs indicate a general trend of increasing LPI with increasing MDCI levels, thus supporting the assumption that LPI is derived from NTBI.

Specifically, these results (FIG. 16C) suggest that more than 50% of MDS treated patients develop NTBI forms including MDCI and LPI. This population of usually elderly people is examined on a monthly basis. In Israel, where there are about 2,000 of MDS patients, of which 1,000 are under treatment and 500 are likely to have NTBI forms based on a random sample of 13 MDS patients from the hematology Unit of Wolfson Medical Center, Holon in collaboration with Drs Asher Windler and E. Rachmilevich). In the USA there are 120,000 treated MDS patients and about 300,000 worldwide, out of which 150,000 are likely to be NTBI carriers, and some might be candidates for iron chelation therapy. Surveillance of these chronically ill patients, as most others, demands periodic tests, among which those related to NTBI might be also correlated with the health status of the patients.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. AU publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention.

What is claimed is:

1. A method of determining a presence or absence of a disorder associated with abnormal levels of free iron in a biological fluid of a subject, the method comprising:
    (a) obtaining a sample from the biological fluid of the subject;
    (b) exposing said sample to a compound devoid of iron and being capable of binding endogenous apo-Transferrin present in said sample;
    (c) contacting said sample with an indicator including an iron binding moiety attached to a signal generating moiety, said indicator being incapable of binding said compound, wherein an intensity of said signal generated by said signal generating moiety is related to an amount of said iron bound by said iron binding moiety; and
    (d) detecting and quantifying said signal thereby quantifying free iron levels in the biological fluid and determining in the subject a presence or absence of the disorder associated with abnormal free iron levels.

2. The method of claim 1, wherein said intensity of said signal is stoichiometrically related to said iron bound by said iron binding moiety.

3. The method of claim 1, wherein said compound includes Gallium or Cobalt.

4. The method of claim 1, wherein said indicator includes modified apo-transferrin.

5. The method of claim 1, wherein said signal generating moiety is a fluorophore.

6. The method of claim 5, wherein said fluorophore is selected from the group consisting of Fluorescein, Rhodamin, nitrobenzfurazan, fluorogenic β-galactosidase and a green fluorescent protein.

7. The method of claim 1, wherein said signal generating moiety includes a reactive group for binding said iron binding moiety.

8. The method of claim 7, wherein said reactive group is selected from the group consisting of dichlorotriazinyl, isothiocyanate, succinimidyl ester, sulfonyl chloride.

9. The method of claim 1, wherein said iron binding moiety is selected from the group consisting of apo-transferrin, lactoferrin, ovotransferrin, desferrioxamine, phenanthroline, ferritin, porphyrin, ethylene diamine tetra-acetic acid and diethylene triamine-pentaacetic acid.

10. The method of claim 1, further comprising contacting said sample with an apo-transferrin binding metal other than iron prior to step (a).

11. The method of claim 10, wherein said apo-transferrin binding metal other than iron is selected from the group consisting of Gallium and Cobalt.

12. The method of claim 1, further comprising contacting said sample with an iron mobilizing reagent prior to step (a).

13. The method of claim 12, wherein said iron mobilizing reagent is selected from the group consisting of sodium-oxalate, nitrilotriaacetate, ascorbate and salicylate.

14. The method of claim 1, further comprising comparing said signal generated from said sample to said signal generated from a second sample pretreated with an iron chelator prior to step (b).

15. The method of claim 14, wherein said chelator is selected from the group consisting of diethylene triamine-pentaacetic acid, ethylene diamine tetra-acetic acid, N,N'-bis[2-hydroxybenzoyl]ethylene diamine-N,N'-diacetic acid and deferriprone.

16. The method of claim 1, wherein said biological fluid is selected from the group consisting of blood, serum, plasma, lymph, bile fluid, urine, saliva, sputum, tears, cerebrospinal fluid (CSF), bronchioalveolar lavage fluid, synovial fluid, semen, ascites fluid and pus.

17. The method of claim 1, wherein said quantifying said signal is effected by against a calibration curve said calibration curve depicting a fluorescence quenching against known iron concentration.

18. A method of determining a presence or absence of a disorder associated with abnormal levels of free iron in a biological fluid of a subject, the method comprising:
    (a) obtaining a sample from the biological fluid of the subject;
    (b) contacting said sample with an enzyme including an iron binding moiety and signal generating moiety, wherein an intensity of said signal generated by said signal generating moiety is related to an amount of said iron bound by said iron binding moiety; and
    (c) detecting and quantifying said signal thereby quantifying free iron levels in the biological fluid and determining in the subject a presence or absence of the disorder associated with abnormal free iron levels.

19. The method of claim 18, wherein said enzyme is an aconitase enzyme.

20. A method of determining a presence or absence of a disorder associated with abnormal levels of free iron in a biological fluid of a subject, the method comprising:
    (a) obtaining a sample from the biological fluid of the subject;
    (b) removing endogenous apo-Transferrin from said sample via an anti apo-transferrin antibody and/or anionic solid phase;
    (c) contacting said sample with an indicator including an iron binding moiety and signal generating moiety, wherein an intensity of said signal generated by said signal generating moiety is related to an amount of said iron bound by said iron binding moiety; and
    (d) detecting and quantifying said signal thereby quantifying free iron levels in the biological fluid and determining in the subject a presence or absence of the disorder associated with abnormal free iron levels.

* * * * *